United States Patent [19]
Clark et al.

[11] Patent Number: 4,595,690
[45] Date of Patent: Jun. 17, 1986

[54] ANTIHYPERTENSIVE DIHYDROPYRIDINE DERIVATIVES

[75] Inventors: Robin Clark, Palo Alto; Moysey M. Povzhitkov, Mountain View, both of Calif.

[73] Assignee: Syntex (U.S.A.) Inc., Palo Alto, Calif.

[21] Appl. No.: 700,439

[22] Filed: Feb. 11, 1985

[51] Int. Cl.$^4$ .................. C07D 211/90; A61K 31/455
[52] U.S. Cl. ..................................... 514/356; 546/321
[58] Field of Search .................. 546/321; 514/356

[56] References Cited
U.S. PATENT DOCUMENTS

| | | | |
|---|---|---|---|
| 3,985,758 | 10/1976 | Murakami et al. | 260/295.5 |
| 4,031,104 | 6/1977 | Bossert et al. | 260/295.5 |
| 4,044,141 | 8/1977 | Bossert et al. | 424/266 |
| 4,154,839 | 5/1979 | Wehinger et al. | 424/266 |
| 4,162,321 | 7/1979 | Wehinger et al. | 424/266 |

*Primary Examiner*—Henry R. Jiles
*Assistant Examiner*—Dale A. Bjorkman
*Attorney, Agent, or Firm*—Grant D. Green; Tom M. Moran; Alan M. Krubiner

[57] ABSTRACT

Novel dihydropyridine derivatives which are useful for treating congestive heart failure, hypertension, and angina have the formula 1:

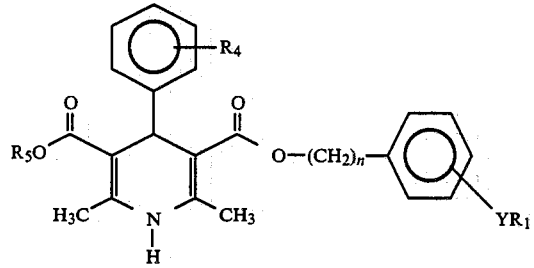

(1)

or a pharmaceutically acceptable acid addition salt thereof, wherein:

n is an integer from 0 to 8;
Y is —O, —NH, —NR$_2$, —S, —S(O), —S(O)$_2$, or a bond;
R$_1$ and R$_2$ are each independently A$_1$, A$_2$, A$_3$ or A$_4$ where:
A$_1$ is —(CH$_2$)$_m$(CHOH)$_p$CH$_2$OH;
A$_2$ is —(CH$_2$)$_q$CH$_{(3-r)}$[(CH$_2$)$_s$OH]$_r$;
A$_3$ is —(CH$_2$)$_q$CH$_{(3-r)}$[(CH$_2$)$_p$COOR$_3$]$_r$; and
A$_4$ is —(CH$_2$)$_m$COOR$_3$; where:
m is an integer from 1 to 8;
p is an integer from 0 to 4;
q is an integer from 0 to 8;
r is 2 or 3;
s is an integer from 1 to 4; and
R$_3$ is H or alkyl of 1 to 18 carbon atoms;
R$_4$ is —NO$_2$, —CF$_3$, or halo; and
R$_5$ is lower alkyl or —CH$_2$CH$_2$OCH$_3$.

23 Claims, No Drawings

ANTIHYPERTENSIVE DIHYDROPYRIDINE DERIVATIVES

BACKGROUND OF THE INVENTION

1. Field of the Invention

This invention relates to 4-phenyl-1,4-phenyl-1,4-dihydropyridine derivatives and the pharmaceutically acceptable acid addition salts thereof which are useful in the treatment of cardiovascular diseases such as hypertension, congestive heart failure, angina, migraine, and vasospastic disorders. The invention also relates to a pharmaceutically acceptable composition containing an effective amount of at least one of the compounds in combination with a suitable excipient, the composition being useful for the treatment of cardiovascular diseases such as hypertension, congestive heart failure, angina, migraine, and vasospastic disorders in mammals. The invention also relates to a process for making the compounds of the invention, and the use of compounds of the invention in pharmaceutical compositions useful for the treatment of cardiovascular diseases such as hypertension, congestive heart failure, angina, migraine, and vasospastic disorders in mammals.

2. Related Disclosures

Certain 4-phenyl-1,4-dihydropyridine derivatives are known. See, for example, U.S. Pat. Nos. 3,485,847 and 4,044,141. A novel class of 4-phenyl-1,4-dihydropyridine derivatives has now been prepared.

SUMMARY OF THE INVENTION

The first aspect of this invention is the group of compounds represented by the formula

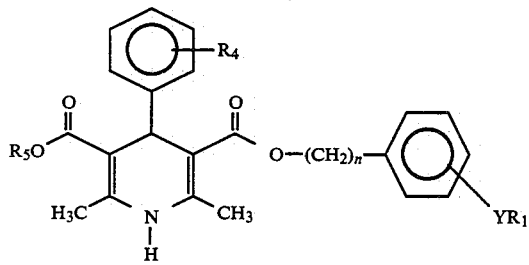

(1)

or a pharmaceutically acceptable acid addition salt thereof, wherein:

n is an integer from 0 to 8;
Y is —O, —NH, —NR$_2$, —S, —S(O), —S(O)$_2$, or a bond;
R$_1$ and R$_2$ are each independently A$_1$, A$_2$, A$_3$ or A$_4$ where
A$_1$ is —(CH$_2$)$_m$(CHOH)$_p$CH$_2$OH;
A$_2$ is —(CH$_2$)$_q$CH$_{(3-r)}$[(CH$_2$)$_s$OH]$_r$;
A$_3$ is —(CH$_2$)$_q$CH$_{(3-r)}$[(CH$_2$)$_p$COOR$_3$]$_r$; and
A$_4$ is —(CH$_2$)$_m$COOR$_3$; where
  m is an integer from 1 to 8;
  p is an integer from 0 to 4;
  q is an integer from 0 to 8;
  r is 2 or 3;
  s is an integer from 1 to 4; and
  R$_3$ is H or alkyl of 1 to 18 carbon atoms;
R$_4$ is —NO$_2$, —CF$_3$, or halo; and
R$_5$ is lower alkyl or —CH$_2$CH$_2$OCH$_3$.

Another aspect of the invention is a composition useful in the treatment of cardiovascular diseases such as hypertension, congestive heart failure, angina, migraine, and vasospastic disorders in mammals, which composition comprises an effective amount of at least one compound chosen from those represented by formula 1 above or a pharmaceutically acceptable acid addition salt thereof and a pharmaceutically suitable excipient.

Still another aspect of the invention is a method for treating cardiovascular diseases such as hypertension, congestive heart failure, angina, migraine, and vasospastic disorders in mammals which comprises administering an effective amount of at least one compound chosen from those represented by formula 1 above.

Still another aspect of the invention is a process for making the compounds of formula 1.

Still another aspect of the invention is the use of a compound of formula 1 to form a pharmaceutical composition for the treatment of cardiovascular diseases such as hypertension, congestive heart failure, angina, migraine, and vasospastic disorders in mammals.

DETAILED DESCRIPTION AND PREFERRED EMBODIMENTS

The broadest aspect of the present invention is the group of compounds represented by the formula

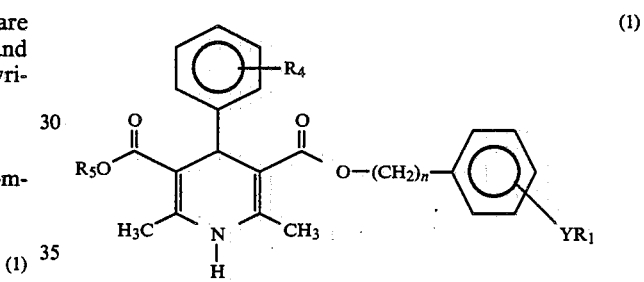

(1)

or a pharmaceutically acceptable acid addition salt thereof, wherein:

n is an integer from 0 to 8;
Y is —O, —NH, —NR$_2$, —S, —S(O), —S(O)$_2$, or a bond;
R$_1$ and R$_2$ are each independently A$_1$, A$_2$, A$_3$ or A$_4$ where:
A$_1$ is —(CH$_2$)$_m$(CHOH)$_p$CH$_2$OH;
A$_2$ is —(CH$_2$)$_q$CH$_{(3-r)}$[(CH$_2$)$_s$OH]$_r$;
A$_3$ is —(CH$_2$)$_q$CH$_{(3-r)}$[(CH$_2$)$_p$COOR$_3$]$_r$; and
A$_4$ is —(CH$_2$)$_m$COOR$_3$; where
  m is an integer from 1 to 8;
  p is an integer from 0 to 4;
  q is an integer from 0 to 8;
  r is 2 or 3;
  s is an integer from 1 to 4; and
  R$_3$ is H or alkyl of 1 to 18 carbon atoms;
R$_4$ is —NO$_2$, —CF$_3$, or halo; and
R$_5$ is lower alkyl or —CH$_2$CH$_2$OCH$_3$.

One preferred subgenus of compounds of formula 1 is that wherein R$_4$ is meta —NO$_2$, particularly where R$_5$ is methyl, and more particularly where Y is para —O. A particularly preferred compound is that in which R$_1$ is A$_1$, m and p are both 1, and n is 2. Another preferred compound is that in which n is 1.

Another preferred subgenus of compounds of formula 1 is that wherein R$_4$ is meta —NO$_2$, R$_5$ is methyl, Y is para —O, R$_1$ is A$_2$, and n is 2. A preferred compound is that wherein q is 0, r is 2, and s is 1.

Another preferred subgenus of compounds of formula 1 is that wherein R$_4$ is meta —NO$_2$, R$_5$ is methyl, Y is para —NH, $R_1$ is $A_1$, and n is 2. A preferred compound is that wherein m is 1, and p is 0.

Another preferred subgenus of compounds of formula 1 is that wherein $R_4$ is meta —$NO_2$, $R_5$ is methyl, Y is para —O, $R_1$ is $A_4$, and n is 2. A preferred compound is that wherein m is 2.

As used in the specification and the appended claims, unless specified to the contrary, the following terms have the meaning indicated:

The term "lower alkyl" refers to a straight or branched chain monovalent substituent consisting solely of carbon and hydrogen, containing no unsaturation and having from one to four carbon atoms. Examples of lower alkyl groups are methyl, ethyl, n-propyl, i-propyl, n-butyl, i-butyl, s-butyl and t-butyl.

The term "halo" as used herein refers to chloro, bromo and iodo.

The term "protecting group" refers to a group that is used to prevent hydroxy or carbonyl groups from reacting prematurely during the preparation of compounds of the invention. Examples of protecting groups are benzyl ethers, acetonides, and esters. Protecting groups are ideally easily applied and removed under conditions unlike the reaction conditions used in the preparations. For example, benzyl ethers are stable under the acidic and basic conditions used in preparation of compounds of formula 1, but are easily removed using $H_2$ over Pd/C.

The term "pharmaceutically acceptable acid addition salts" refers to salts of the subject compounds which possess the desired pharmacological activity and which are neither biologically nor otherwise undesirable. These salts are formed with inorganic acids such as hydrochloric acid, hydrobromic acid, sulfuric acid, nitric acid or phosphoric acid; or organic acids such as acetic acid, propionic acid, glycolic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid and the like.

The term "treatment" as used herein covers any treatment of a disease in a mammal, particularly a human, and includes:

(i) preventing the disease from occurring in a subject which may be predisposed to the disease but has not yet been diagnosed as having it;

(ii) inhibiting the disease, i.e., arresting its development; or (iii) relieving the disease, i.e., causing regression of the disease.

Certain compounds of formula 1 in which $R_1$ or $R_2$ is asymmetric may form optical isomers. In the compounds of the invention, any isomer or mixture of isomers may be used. The isomers may be separated by various methods, for example selective crystallization and column chromatography. Alternatively, the compounds of the invention may be prepared using optically active reactants. (The invention includes all optical isomers of any asymmetric compound of formula 1, as well as mixtures thereof.)

The nomenclature used herein is basically a modified form of I.U.P.A.C. Compounds of the invention are named as derivatives of 1,4-dihydropyridine. The positions in the compounds are numbered beginning with the pyridine nitrogen and proceeding clockwise in all drawings of the structure. For example, the following compound is named 2,5-dimethyl-3-methoxycarbonyl-4-(3-nitrophenyl)-5-(2-[4-(2,3-dihydroxypropoxy)-phenyl]ethoxycarbonyl)-1,4-dihydropyridine:

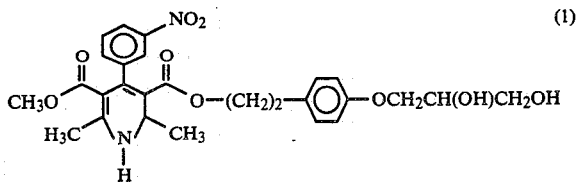

(1)

ADMINISTRATION AND FORMULATION

Another aspect of the present invention relates to pharmaceutical compositions useful in the treatment of cardiovascular diseases such as hypertension, congestive heart failure, angina, migraine, and vasospastic disorders, particularly in the treatment of hypertension in a mammalian subject, comprising a therapeutically effective amount of a compound of formula 1, or a pharmaceutically acceptable acid addition salt thereof, in admixture with a pharmaceutically acceptable non-toxic carrier. A therapeutically effective amount is that amount which, when administered to a mammal in need thereof, is sufficient to effect treatment, as defined above. Thus, the level of the drug in the formulation can vary from about 5 percent weight (%w) to about 95%w of the drug based on the total formulation and about 5%w to 95%w excipient. Preferably the drug is present at a level of about 10%w to about 70%w.

Useful pharmaceutical carriers for the preparation of the pharmaceutical compositions hereof can be solids or liquids. Thus, the compositions can take the form of tablets, pills, capsules, powders, sustained release formulations, solutions, suspensions, elixirs, aerosols, and the like. Carriers can be selected from the various oils, including those of petroleum, animal, vegetable or synthetic origin, for example, peanut oil, soybean oil, mineral oil, sesame oil, and the like. Water, saline, aqueous dextrose, and glycols are preferred liquid carriers, particularly for injectable solutions. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. Other suitable pharmaceutical carriers and their formulations are described in "Remington's Pharmaceutical Sciences" by E. W. Martin.

Another aspect of the present invention relates to a method for treating cardiovascular diseases such as hypertension, congestive heart failure, angina, migraine, and vasospastic disorders in a mammalian subject (particularly a human) which method comprises administering a therapeutically effective amount of a compound of formula 1, or a pharmaceutically acceptable acid addition salt thereof, to a mammal in need thereof.

In the practice of the above described method of the present invention a therapeutically effective amount of the compound of formula 1 or a pharmaceutical composition containing same is administered via any of the usual and acceptable methods known in the art, either singly or in combination with another compound or compounds of the present invention or other pharmaceutical agents. These compounds or compositions can thus be administered orally, systemically (e.g., transdermally, intranasally or by suppository) or parenterally (e.g., intramuscularly, subcutaneously and intravenously), and can be administered either in the form of solid or liquid dosages including tablets, solutions, suspensions, aerosols, and the like, as discussed in more detail above. It is preferred to administer compounds of formula 1 orally.

The formulation can be administered in a single unit dosage form for continuous treatment or in a single unit dosage form ad libitum when relief of symptoms is specifically required.

The Spontaneously Hypertensive Rat (SHR) assay is an accepted test for determining antihypertensive activity. See, e.g., J. Roba, et al., *Arch. Int. Pharmacodyn.*, 200, 182 (1972). The compounds of the invention exhibit antihypertensive activity in the SHR assay.

Other accepted tests for cardiovascular activity include ultrasonic two-dimensional echocardiography and anesthetized dog assays. See, e.g., P. Gueret, M.D., et al., *Circulation*, 62(6), 1308 (1980), and M. Tripp, *American J. of Physiology*, 232(2), H173 (1977), respectively. The compounds of the invention demonstrate positive activity in these assays, also.

In view of the foregoing as well as in consideration of the degree of severity of the condition being treated, age of subject and so forth, all of which factors are determinable by routine experimentation by one skilled in the art, the effective dosage in accordance herewith can vary over a wide range. Generally, a therapeutically effective amount ranges from about 1.0 to about 1000 μg/kg body weight per day and preferably, for example, for antihypertensive use, from about 30 to about 500 μg/kg body weight per day. In alternative terms, for an average 70 kg adult human subject, a therapeutically effective amount in accordance herewith would be, in preferred embodiments from about 70 μg to about 7000 μg per day per subject, and preferably from about 2100 μg to 3500 μg per day per subject.

PREPARATION OF THE INVENTION

Compounds of formula 1 are prepared by the reaction sequence shown below.

SCHEME 1

(Step 1)

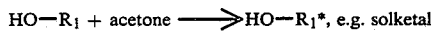
HO—R$_1$ + acetone ⟶ HO—R$_1$*, e.g. solketal (Step 2)

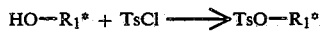
HO—R$_1$* + TsCl ⟶ TsO—R$_1$*

(Step 3)

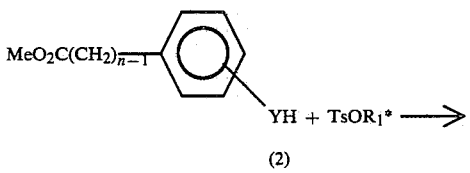
(2)

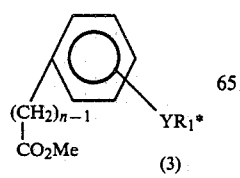
(3)

(Step 4)

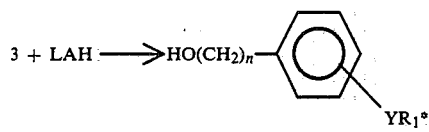
3 + LAH ⟶ HO(CH$_2$)$_n$—⟨ring⟩—YR$_1$*

(Step 5)

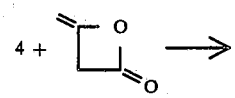

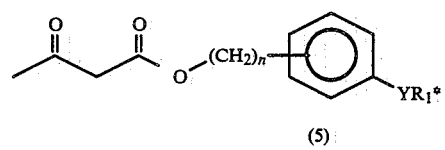
(5)

(Step 6)

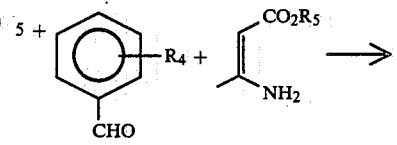

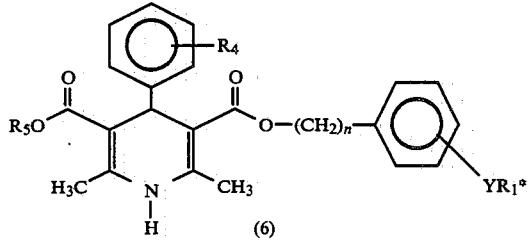
(6)

(Step 7)

6 ⟶

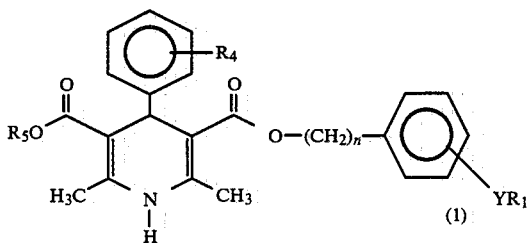
(1)

SCHEME 2

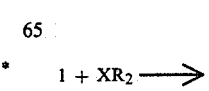
1 + XR$_2$ ⟶

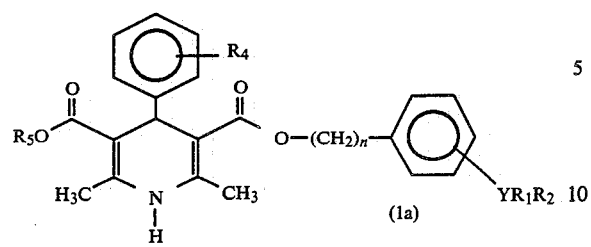
(1a)
SCHEME 3
(Step 1)
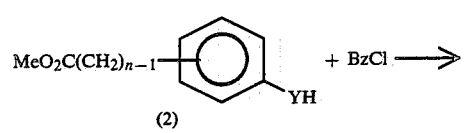
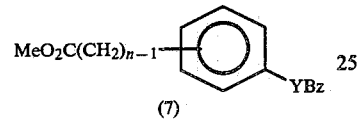
(Step 2)
7 ⟶ 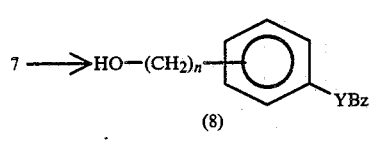
(Step 3)
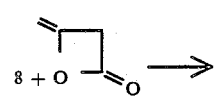 ⟶
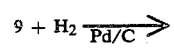
(Step 4)
9 + H₂ $\xrightarrow{\text{Pd/C}}$
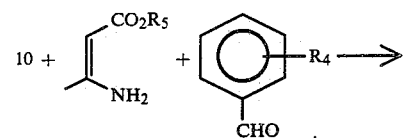
(Step 5)
10 + $\underset{\underset{NH_2}{|}}{\overset{\overset{CO_2R_5}{|}}{C}}=CH-CH_3$ + (phenyl with R₄ and CHO) ⟶
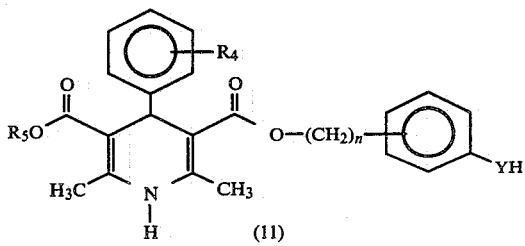
(11)
(Step 6)
11 + R₁* ⟶
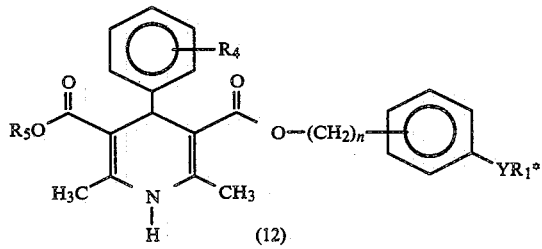
(12)
(Step 7)
12 + R₂* ⟶
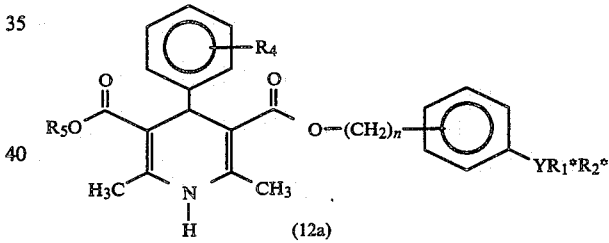
(12a)
(Step 8)
12 or 12a ⟶ 1
SCHEME 4
(Step 1)
(phenyl)-Y(CH₂)$_q$X + $\underset{O}{\overset{O}{\|}}$CH₂(COOEt)₂ ⟶
*O(CH₂)$_n$—(phenyl)—Y(CH₂)$_q$—CH(COOEt)₂
(14)
(Step 2)

-continued

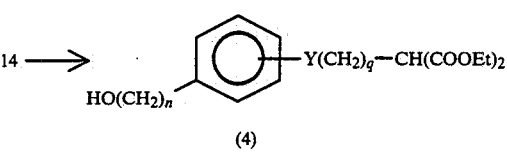

(4)

In the above Schemes, $R_1$, $R_2$, $R_3$, $R_4$, $R_5$, and Y are as described above in the broadest scope of the invention. Additionally, R is lower alkyl, Ts is tosyl, X is chloro or bromo, Bz is benzyl, and * denotes a protecting group.

Compounds in which Y is —O, —NH, —NR$_2$, —S, or —S(O)$_{1,2}$ and $R_1$ is $A_1$ or $A_2$ are prepared according to Scheme 1.

A suitable alkanol is selected to form the desired $R_1$. The alkanol may have two or more —OH groups. For compounds in which $R_1$ is $A_1$, sugars are a convenient source of optically pure alkanols. The appropriate —OH groups are protected by means known in the art, especially by forming acetonides and benzyl ethers. In the Schemes, protected $R_1$ and Y radicals are indicated by asterisks, e.g., $R_1^*$, $Y^*$. (Step 1.)

The protected alkanol is then reacted with tosyl chloride or a similar electrophile under basic conditions to produce a tosylate or a similar molecule with an advantageous leaving group. (Step 2.)

The tosylate is reacted with an appropriate methyl ω-phenylalkylcarboxylate derivative (2) under basic catalysis, e.g., using sodium hydride in dimethyl formamide (DMF) to form an alkylated ω-phenylalkylcarboxylate derivative (3). Compounds of formula 2 in which Y is —O, —NH, or —S are known and are commercially available from, e.g., Aldrich chemical Co. For example, methyl (4-hydroxyphenyl)acetate is used when compounds of formula 1 in which n=2, Y=para —OR$_1$, are desired. (Step 3.)

The carboxylate compound 3 is then reduced, e.g. by lithium aluminum hydride (LAH), to a hydroxyalkylbenzene derivative (4), for example, 1-(2-hydroxyethyl)-4-(2-benzyloxyethoxy)benzene. (Step 4.)

Diketene (3-buteno-β-lactone, available, e.g., from Aldrich Chemical Co.) is then added to the hydroxyalkylbenzene derivative 4 under basic conditions, e.g., using triethylamine in dimethoxyethane (DME) to form a ω-phenylalkylacetoacetate derivative (5). For example, 1-(2-hydroxyethyl)-4-(2-benzyloxyethoxy)benzene is reacted with diketene to afford 2-[4-(2-benzyloxyethoxy)phenyl]ethylacetoacetate (5). (Step 5.)

The ω-phenylalkylacetoacetate derivative (5) is then reacted with an alkyl β-aminocrotonate (or methoxyethyl β-aminocrotonate depending on the desired $R_5$) and a benzaldehyde derivative (depending on the desired $R_4$, e.g. for compounds in which $R_4$ is meta —NO$_2$, 3-nitrobenzaldehyde is used) under Hantzsch Dihydropyridine synthesis conditions (see, e.g., Fox, et al., J. Org. Chem., 16, 1259 (1951)) to form a 4-phenyl-2,5-dimethyl-1,4-dihydropyridine dicarboxylate diester (6). For example, 2-[4-(2-benzyloxyethoxy)phenyl]ethylacetoacetate (5) is reacted with methyl β-aminocrotonate and 3-nitrobenzaldehyde to produce 2,6-dimethyl-3-methoxycarbonyl-4-(3-nitrophenyl)-5-(2-[4-(2-benzyloxyethoxy)phenyl]ethoxycarbonyl)-1,4-dihydropyridine. (Step 6.)

The dihydropyridine derivative (6) may then be converted to a compound of formula 1 by removing the protecting groups. Compounds of the invention which are protected by ketal formation are active without deprotection. If the hydroxy radicals were protected by ketal formation, deprotection may be accomplished using a dilute strong acid. For example, acetonides may be removed by treatment with 5% HCl in a protic solvent, preferably water, in a temperature range from 0°-120° C., preferably about 100° C. If benzyl ethers have been employed, deprotection may be achieved by catalytic reduction, e.g. by using H$_2$ and Pd/C at pressures between 10-200 psi. For example, 2,6-dimethyl-3-methoxycarbonyl-4-(3-nitrophenyl)-5-(2-[4-(2-benzyloxyethoxy)-phenyl]ethoxycarbonyl)-1,4-dihydropyridine may be reduced with H$_2$ over 10% Pd/C at 50 psi to afford 2,6-dimethyl-3-methoxycarbonyl-4-(3-nitrophenyl)-5-(2-[4-(2-hydroxyethoxy)phenyl]ethoxycarbonyl)-1,4-dihydropyridine (1). (Step 7.)

When compounds in which Y is —NR$_2$ are desired, a compound of formula 1 (Y=—NH), e.g., obtained through Scheme 1 may be directly alkylated with, e.g., 2-bromoethanol, to afford a dialkylamino compound of formula 1a. For example, 2-bromoethanol may be reacted with 2,6-dimethyl-3-methoxycarbonyl-4-(3-nitrophenyl)-5-(2-[4-(2-hydroxyethylamino)phenyl]ethoxycarbonyl)-1,4-dihydropyridine (1, Y=—NH) to form 2,6-dimethyl-3-methoxycarbonyl-4-(3-nitrophenyl)-5-(2-[4-N,N-(2-hydroxyethyl)amino]phenylethoxycarbonyl)-1,4-dihydropyridine (1a). (Scheme 2.)

Compounds of formula 1 in which Y is —S(O) or —S(O)$_2$ may be made from compounds of formula 1 in which Y is —S by oxidation. For example, 2,6-dimethyl-3-methoxycarbonyl-4-(3-nitrophenyl)-5-(2-[4-(2-hydroxyethylthio)phenyl]ethoxycarbonyl)-1,4-dihydropyridine (1, Y=—S) may be reacted with hydrogen peroxide in acetone to form 2,6-dimethyl-3-methoxycarbonyl-4-(3-nitrophenyl)-5-(2-[4-(2-hydroxyethylsulfinyl)phenyl]ethoxycarbonyl)-1,4-dihydropyridine (1, Y=—S(O)). Similarly, 2,6-dimethyl-3-methoxycarbonyl-4-(3-nitrophenyl)-5-(2-[4-(2-hydroxyethylsulfinyl)phenyl]ethoxycarbonyl)-1,4-dihydropyridine (1, Y=—S(O)) may be treated with peroxyacetic acid in acetone to yield 2,6-dimethyl-3-methoxycarbonyl-4-(3-nitrophenyl)-5-(2-[4-(2-hydroxyethylsulfonyl)phenyl]-ethoxycarbonyl)-1,4-dihydropyridine (1, Y=—S(O)$_2$).

Compounds of formula 1 in which $R_1$ is $A_1$ or $A_2$ may be converted to compounds in which $R_1$ is $A_3$ or $A_4$ by oxidation of the hydroxy groups to carboxylic acid groups, followed by esterification where desired. (Scheme 2.)

Compounds of formula 1 may also be prepared by the procedure of Scheme 3, which differs from Scheme 1 in that the dihydropyridine nucleus is formed first, followed by deprotection and alkylation of Y with $R_1^*$, followed by deprotection of $R_1^*$.

Compounds of formula 1 may also be prepared by the variation set out in Scheme 4, especially where Y is a bond. A haloalkylphenylalkanol ether of formula 13 may be alkylated, e.g., with diethyl malonate using sodium ethoxide in ethanol. The resulting alkylphenylalkanol ether (14) may then be converted to a compound of formula 4 by removal of the alkyl ether moiety R. The synthesis of a compound of formula 1 is then completed according to Scheme 1.

Pharmaceutically acceptable acid addition salts of the compounds of formula 1 are prepared by reacting a free base of formula 1 with an appropriate acid. Free bases of formula 1 are prepared by reacting an acid addition salt of a compound of formula 1 with an appropriate base.

In summary, compounds of formula 1 are prepared by the following method:

Compounds of formula 1 in which $R_1$ or $R_2$ is $A_1$ or $A_2$ are prepared by deprotecting a compound of formula 6. For compounds protected by ketal formation, deprotection is accomplished by reacting a compound of formula 6 with a dilute acid in a protic solvent or mixture of solvents to form an unprotected compound of formula 1. These reactions are carried out at atmospheric pressure at temperatures between the freezing and boiling points of the solvent employed, preferably between 0° and 120° C., and most preferably at about 100° C. Compounds protected by benzyl ether formation are deprotected by catalytic reduction using hydrogen. These reactions are carried out at pressures of 10–200 psi, preferably at about 50 psi, using noble metal catalysts, preferably 10% palladium on carbon.

Compounds of formula 1 in which $R_1$ is $A_3$ or $A_4$ are also prepared by deprotecting a compound of formula 6. For compounds of formula 1 in which $R_3$ is —H, deprotection may be effected by treating a compound of formula 6 with a catalytic amount of a strong acid in a stoichiometric excess of water. For compounds of formula 1 in which $R_3$ is alkyl, a compound of formula 6 is treated with a catalytic amount of a strong acid in a stoichiometric excess of an alcohol of formula $R_3OH$. (The alcohol of formula $R_3OH$ may also serve as the solvent.) These reactions are typically performed at ambient pressure, at temperatures between the boiling and freezing points of the solvent, preferably between 25° and 100° C.

The following specific description is given to enable those skilled in the art to more clearly understand and practice the invention. It should not be considered as a limitation upon the scope of the invention, but merely as being illustrative and representative thereof.

PREPARATION 1

(Protection of Starting Materials; $R_1^*$)

(A) For compounds in which $R_1$ is of the formula $A_1$ with m=1, p=1, it is convenient to use solketal (2,2-dimethyl-4-hydroxymethyl-1,3-dioxolane), which is commercially available from, e.g., Aldrich Chemical Co.

Solketal may also be prepared by the following procedure:

1,2,3-propyltriol (18 g, 0.2 mol) is added to 20 ml of acetone, 40 ml of benzene, and 1 ml $H_2SO_4$ and heated at reflux for 2 h using a Dean-Stark trap. The resulting solketal is added to aqueous NaOH, extracted with ether, and purified by silica gel chromatography.

(B) Similarly, proceeding as in part A above but substituting 1,2,4-butatriol (m=2, p=1), 1,2,5-pentatriol (m=3, p=1), or 1,2,3,4-butatetrol (m=1, p=2) for 1,2,3-propyltriol, the following compounds are prepared:

2,2-dimethyl-4-(2-hydroxyethyl)-1,3-dioxolane;
2,2-dimethyl-4-(3-hydroxypropyl)-1,3-dioxolane;
2,2-dimethyl-4,5-di(hydroxymethyl)-1,3-dioxolane.

(C) Alternatively, benzyl ethers may be used to protect —OH groups. For example, 2,2-dimethyl-4,5-di(hydroxymethyl)-1,3-dioxolane (8 g, 0.2 mol) is heated at reflux with benzyl chloride (25 g, 0.2 mol) and $K_2CO_3$ (25 g, 0.2 mol) in 100 ml ethanol. The product is added to aqueous NaOH, extracted with ether, and purified by silica gel chromatography to yield 2,2-dimethyl-4-hydroxymethyl-5-benzyloxymethyl-1,3-dioxolane.

(D) Similarly, proceeding as in part C above but substituting ethylene glycol or 1,3-propyldiol for 2,2-dimethyl-4,5-di(hydroxymethyl)-1,3-dioxolane, the following compounds may be prepared:

2-benzyloxyethanol;
3-benzyloxypropan-1-ol.

PREPARATION 2

(Preparation of $R_1^*$ Tosylates)

(A) 2,2-Dimethyl-4-hydroxymethyl-1,3-dioxolane (26 g, 0.2 mol) is added to 38 g of p-toluenesulfonyl chloride (0.2 mol) in 200 ml of pyridine and allowed to stand at 0° C. for 24 h. Water was added, and the mixture extracted with ethyl acetate. The ethyl acetate extract was washed with water and brine, dried over $Na_2SO_4$, and evaporated to yield 2,2-dimethyl-4-tosyloxymethyl-1,3-dioxolane.

(B) Similarly, proceeding as in part A above but substituting the compounds prepared in Preparation 1 (B-D), 1,3-dibenzyloxypropan-2-ol or 5-hydroxymethyl-2,2-dimethyl-1,3-dioxane for 2,2-dimethyl-4-hydroxymethyl-1,3-dioxolane, the following compounds are prepared:

2,2-dimethyl-4-(2-tosyloxyethyl)-1,3-dioxolane;
2,2-dimethyl-4-(3-tosyloxypropyl)-1,3-dioxolane;
2,2-dimethyl-4-tosyloxymethyl-5-benzyloxymethyl-1,3-dioxolane;
1-benzyloxy-2-tosyloxyethane;
1-benzyloxy-3-tosyloxypropane;
1,3-dibenzyloxy-2-tosyloxypropane;
5-tosyloxymethyl-2,2-dimethyl-1,3-dioxane.

PREPARATION 3

(Compounds of Formula 3)

(A) Sodium hydride (4.8 g of 50% mineral oil dispersion, 0.1 mol) was added to a solution of 16.6 g (0.1 mol) of methyl 4-hydroxyphenylacetate (2) (available, e.g., from Aldrich Chemical Co.) in 150 ml of DMF and the mixture stirred for 15 min. Solketal tosylate (28.6 g, 0.1 mol, also available e.g., from Aldrich Chemical Co.) was added and the solution stirred at 70° C. for 12 hr. The mixture was added to 500 ml of water and extracted with ether to afford 27 g of crude methyl 4-(2,2-dimethyl-1,3-dioxolan-4-yl)methoxyphenylacetate (3) (Y=—O, n=2) as an oil which was used in subsequent steps without purification.

(B) Similarly, by following the procedure of part (A) above, but substituting the compounds prepared in Preparation 2 for solketal tosylate, the following compounds (Y=—O) are prepared:

methyl 4-[2-(2,2-dimethyl-1,3-dioxolan-4-yl)-ethoxy]-phenylacetate (m=2, p=1);
methyl 4-[3-(2,2-dimethyl-1,3-dioxolan-4-yl)-propyloxy]phenylacetate (m=3, p=1);
methyl 4-(2,2-dimethyl-5-benzyloxymethyl-1,3-dioxolan-4-yl)methoxyphenylacetate (m=1, p=2);
methyl 4-(2-benzyloxyethoxy)phenylacetate (m=1, p=0);
methyl 4-(3-benzyloxypropoxy)phenylacetate (m=2, p=0);
methyl 4-(1,3-dibenzyloxypropyl-2-oxy)phenylacetate;
methyl 4-(2,2-dimethyl-1,3-dioxan-5-yl)oxymethylphenylacetate.

(C) Similarly, by following the procedure of parts (A) and (B) above, but substituting the compounds prepared in Preparation 2 for solketal tosylate and substituting methyl 4-aminophenylacetate for methyl 4-hydroxyphenylacetate, the following compounds (Y=—NH) are prepared:

methyl 4-(2,2-dimethyl-1,3-dioxolan-4-yl)methylaminophenylacetate (n=2);
methyl 4-[2-(2,2-dimethyl-1,3-dioxolan-4-yl)ethylamino]phenylacetate (m=2, p=1);
methyl 4-[3-(2,2-dimethyl-1,3-dioxolan-4-yl)propylamino]phenylacetate (m=3, p=1);
methyl 4-(2,2-dimethyl-5-benzyloxymethyl-1,3-dioxolan-4-yl)methylaminophenylacetate (m=1, p=2);
methyl 4-(2-benzyloxyethylamino)phenylacetate (m=1, p=0);
methyl 4-(3-benzyloxypropylamino)phenylacetate (m=2, p=0);
methyl 4-(1,3-dibenzyloxypropyl-2-amino)phenylacetate;
methyl 4-(2,2-dimethyl-1,3-dioxan-5-yl)aminomethylphenylacetate.

(D) Similarly, by following the procedure of parts (A) and (B) above, but substituting the compounds prepared in Preparation 2 for solketal tosylate and substituting methyl 4-mercaptophenylacetate for methyl 4-hydroxyphenylacetate, the following compounds (Y=—S) are prepared:

methyl 4-(2,2-dimethyl-1,3-dioxolan-4-yl)methylthiophenylacetate (n=2);
methyl 4-[2-(2,2-dimethyl-1,3-dioxolan-4-yl)-ethylthio]phenylacetate (m=2, p=1);
methyl 4-[3-(2,2-dimethyl-1,3-dioxolan-4-yl)-propylthio]phenylacetate (m=3, p=1);
methyl 4-(2,2-dimethyl-5-benzyloxymethyl-1,3-dioxolan-4-yl)methylthiophenylacetate (m=1, p=2);
methyl 4-(2-benzyloxyethylthio)phenylacetate (m=1, p=0);
methyl 4-(3-benzyloxypropylthio)phenylacetate (m=2, p=0);
methyl 4-(1,3-dibenzyloxypropyl-2-thio)phenylacetate;
methyl 4-(2,2-dimethyl-1,3-dioxan-5-yl)thiomethylphenylacetate.

(E) Similarly, by following the procedure of part (A) above, but substituting methyl 3-(4-hydroxyphenyl)propionate and methyl 4-(4-hydroxyphenyl)butanoate for methyl 4-hydroxyphenylacetate, the following compounds are prepared:

methyl 3-[4-(2,2-dimethyl-1,3-dioxolan-4-yl)methoxyphenyl]propionate;
methyl 4-[4-(2,2-dimethyl-1,3-dioxolan-4-yl)methoxyphenyl]butanoate.

PREPARATION 4

(Compounds of Formula 3 in which Y is —S(O)$_{1,2}$)

(A) Compounds of formula 3 in which Y is —S(O) may be prepared from compounds of formula 3 in which Y is —S.

A solution of 1.0 g of methyl 4-(2,2-dimethyl-1,3-dioxolan-4-yl)methylthiophenylacetate (3, Y=—S) and an equimolar amount of 30% hydrogen peroxide in 12 ml of acetone is allowed to stand for 12 h at 25° C. The product methyl 4-(2,2-dimethyl-1,3-dioxolan-4-yl)methylsulfinylphenylacetate (3, Y=—S(O)) is purified by silica gel chromatography.

(B) Similarly, proceeding as in part A above but substituting the compounds prepared in Preparation 3(D) for methyl 4-(2,2-dimethyl-1,3-dioxolan-4-yl)methylthiophenylacetate, the following compounds are prepared:

methyl 4-[2-(2,2-dimethyl-1,3-dioxolan-4-yl)-ethylsulfinyl]phenylacetate (m=2, p=1);
methyl 4-[3-(2,2-dimethyl-1,3-dioxolan-4-yl)-propylsulfinyl]phenylacetate (m=3, p=1);
methyl 4-(2,2-dimethyl-5-benzoyloxymethyl-1,3-dioxolan-4-yl)methylsulfinylphenylacetate (m=1, p=2);
methyl 4-(2-benzyloxyethylsulfinyl)phenylacetate (m=1, p=0);
methyl 4-(3-benzyloxypropylsulfinyl)phenylacetate (m=2, p=0);
methyl 4-(1,3-dibenzyloxypropyl-2-sulfinyl)phenylacetate;
methyl 4-(2,2-dimethyl-1,3-dioxan-5-yl)sulfinylmethylphenylacetate.

(C) Compounds of formula 3 in which Y is —S(O)$_2$ may be prepared from compounds of formula 3 in which Y is —S(O).

A solution of 1.0 g of methyl 4-(2,2-dimethyl-1,3-dioxolan-4-yl)methylsulfinylphenylacetate (3, Y=—S) and an equimolar amount of 30% hydrogen peroxide in 12 ml of 50% acetic acid is allowed to stand for 12 h at 25° C. The product methyl 4-(2,2-dimethyl-1,3-dioxolan-4-yl)methylsulfonylphenylacetate (3, Y=—S(O)$_2$) is purified by silica gel chromatography.

(D) Similarly, proceeding as in part (C) above but substituting the compounds prepared in part (B) above for methyl 4-(2,2-dimethyl-1,3-dioxolan-4-yl)methylsulfinylphenylacetate, the following compounds are prepared:

methyl 4-[2-(2,2-dimethyl-1,3-dioxolan-4-yl)-ethylsulfonyl]phenylacetate (m=2, p=1);
methyl 4-[3-(2,2-dimethyl-1,3-dioxolan-4-yl)-propylsulfonyl]phenylacetate (m=3, p=1);
methyl 4-(2,2-dimethyl-5-benzyloxymethyl-1,3-dioxolan-4-yl)methylsulfonylphenylacetate (m=1, p=2);
methyl 4-(2-benzyloxyethylsulfonyl)phenylacetate (m=1, p=0);
methyl 4-(3-benzyloxypropylsulfonyl)phenylacetate (m=2, p=0);
methyl 4-(1,3-dibenzyloxypropyl-2-sulfonyl)phenylacetate; and
methyl 4-(2,2-dimethyl-1,3-dioxan-5-yl)sulfonylmethylphenylacetate.

PREPARATION 5

(Preparation of Alcohols, 4)

(A) A solution of 27 g (0.096 mol) of methyl 4-(2,2-dimethyl-1,3-dioxolan-4-yl)methoxyphenylacetate (3) in 200 ml of tetrahydrofuran (THF) was added slowly to a stirred suspension of 4.0 g of LAH in 300 ml of THF. The mixture was stirred 2 h at room temperature and then treated sequentially with 4 ml of water, 4 ml of 15% NaOH solution, and 12 ml of water. The mixture was filtered and the filtrate evaporated to a residue which was triturated with hexane to afford 24 g of 4-(2,2-dimethyl-1,3-dioxolan-4-yl)methoxyphenylethan-2-ol (4) as a tan solid.

(B) Similarly, by following the procedure of part (A) above, but substituting compounds prepared in Preparations 3-4 for methyl 4-(2,2-dimethyl-1,3-dioxolan-4-yl)methoxyphenylacetate, the following compounds are prepared:

4-[2-(2,2-dimethyl-1,3-dioxolan-4-yl)ethoxy]phenylethan-2-ol;

4-[3-(2,2-dimethyl-1,3-dioxolan-4-yl)propyloxy]phenylethan-2-ol;
4-(2,2-dimethyl-5-benzyloxymethyl-1,3-dioxolan-4-yl)-methoxyphenylethan-2-ol;
4-(2-benzyloxyethoxy)phenylethan-2-ol;
4-(3-benzyloxypropoxy)phenylethan-2-ol;
4-(1,3-dibenzyloxypropyl-2-oxy)phenylethan-2-ol;
4-(2,2-dimethyl-1,3-dioxan-5-ylmethoxy)phenylethan-2-ol;
4-(2,2-dimethyl-1,3-dioxolan-4-yl)methylaminophenylethan-2-ol;
4-[2-(2,2-dimethyl-1,3-dioxolan-4-yl)ethylamino]-phenylethan-2-ol;
4-[3-(2,2-dimethyl-1,3-dioxolan-4-yl)propylamino]-phenylethan-2-ol;
4-(2,2-dimethyl-5-benzyloxymethyl-1,3-dioxolan-4-yl)-methylaminophenylethan-2-ol;
4-(2-benzyloxyethylamino)phenylethan-2-ol;
4-(3-benzyloxypropylamino)phenylethan-2-ol;
4-(2,2-dimethyl-1,3-dioxolan-4-yl)methylthiophenylethan-2-ol;
4-[2-(2,2-dimethyl-1,3-dioxolan-4-yl)ethylthio]phenylethan-2-ol;
4-(2-benzyloxyethylthio)phenylethan-2-ol;
3-[4-(2,2-dimethyl-1,3-dioxolan-4-yl)methoxyphenyl]-propan-1-ol;
4-[4-(2,2-dimethyl-1,3-dioxolan-4-yl)methoxyphenyl]-butan-1-ol;
4-(2,2-dimethyl-1,3-dioxolan-4-yl)methylsulfinylphenylethan-2-ol;
4-[2-(2,2-dimethyl-1,3-dioxolan-4-yl)ethylsulfinyl]-phenylethan-2-ol ($m=2$, $p=1$);
4-(2-benzyloxyethylsulfinyl)phenylethan-2-ol ($m=1$, $p=0$);
4-(2,2-dimethyl-1,3-dioxolan-4-yl)methylsulfonylphenylethan-2-ol;
4-(2-benzyloxyethylsulfonyl)phenylethan-2-ol ($m=1$, $p=0$).

PREPARATION 6

(Compounds of Formula 4 Wherein Y Is A Bond: Scheme 4)

(A) A solution of 1.0 g 4-(2-bromoethyl)benzoic acid (which may be obtained commercially from e.g., Trans World Chemicals, Inc., or by methods known in the art) and 0.055 g of sodium borohydride in 15 ml of ethanol is stirred for 4 h. The solution is added to 20 ml of water, filtered, and distilled to yield 1-(2-bromoethyl)-4-hydroxymethylbenzene.

The 1-(2-bromoethyl)-4-hydroxymethylbenzene (0.5 g) is then added to a solution of 0.44 g methyl benzenesulfonate and 0.32 g $K_2CO_3$ in 10 ml of methanol and allowed to react for 4 h. The solution is neutralized with methanolic HCl and extracted with ether. The ether extract is dried over $Na_2SO_4$, filtered, and the solvent removed under vacuum to yield 1-(methoxymethyl)-4-(2-bromoethyl)benzene (13).

Diethyl malonate (0.32 g) is added to a solution of 0.05 g sodium in 10 ml of methanol. The 1-(methoxymethyl)-4-(2-bromoethyl)benzene (13) (0.5 g) is then added and allowed to react for 8 h. The solution is neutralized with methanolic HCl and is extracted with ether. The ether extract is dried over $Na_2SO_4$, and evaporated to yield 1-[3,3-di(ethoxycarbonyl)propyl]-4-methoxymethylbenzene (14). The methyl group is removed by treatment with aqueous HBr in acetic acid, followed by neutralization with aqueous NaOH and extraction with ether. The ether extract is dried over $Na_2SO_4$, and evaporated to yield 1-[3,3-di(ethoxycarbonyl)propyl]-4-hydroxymethylbenzene (4).

(B) Similarly, proceeding as in part A above but substituting 4-(2-bromomethyl)benzoic acid, 4-(2-bromomethyl)phenylacetic acid, or 4-(2-bromoethyl)-phenylacetic acid for 4-(2-bromoethyl)benzoic acid, the following compounds are prepared:
1-[3,3-di(ethoxycarbonyl)ethyl]-4-hydroxymethylbenzene;
1-[3,3-di(ethoxycarbonyl)ethyl]-4-(2-hydroxyethyl)-benzene;
1-[3,3-di(ethoxycarbonyl)propyl]-4-(2-hydroxyethyl)-benzene.

(C) Similarly, proceeding as in part A above but substituting diethyl(3-ethoxycarbonyl)malonate for diethyl malonate, the following compound ($R_1=A_3$, $r=3$) is produced:
1-[3,3,3-tri(ethoxycarbonyl)propyl]-4-hydroxymethylbenzene.

Diethyl(3-ethoxycarbonyl)malonate may be prepared as follows:

23.9 g of diethyl bromomalonate (available commercially from, e.g., Aldrich Chemical Co.) is reacted with 2.4 g of dry magnesium turnings in 300 ml of dry ether under nitrogen at $-10°$ C. Dry $CO_2$ is then bubbled through the solution until no more is absorbed. The solution is neutralized with 25% aqueous $H_2SO_4$, extracted with ether, and dried over $Na_2SO_4$. The ether is removed under vacuum, and the residue esterified with 1 ml $H_2SO_4$ and 100 ml of ethanol. The solution is neutralized, extracted with ether, dried over $Na_2SO_4$, and the solvent removed under reduced pressure to yield diethyl(3-ethoxycarbonyl)malonate.

PREPARATION 7

(Chain Extension)

(A) It may be convenient to prepare compounds of formula 14 in which $R_1$ is $A_3$ and p is <0 from compounds of formula 14 in which $R_1$ is $A_3$ and p is 0 by the following method:

A solution of 29.6 g (0.096 mol) of 1-[3,3-di(ethoxycarbonyl)propyl]-1-methoxymethylbenzene (14, $p=0$) in 200 ml of THF is added slowly to a stirred suspension of 4.0 g of LAH in 300 ml of THF. The mixture is stirred 2 h at room temperature and then treated sequentially with 4 ml of water, 4 ml of 15% NaOH solution, and 12 ml of water. The mixture is filtered and the filtrate evaporated to a residue which is triturated with hexane to afford 1-[3,3-di(hydroxymethyl)propyl]-1-methoxymethylbenzene.

The product is then reacted with 17.5 g of $PBr_3$ in 100 ml of ether at 0° C. for 4 h. The solution is filtered, washed with water, and the ether layer dried over $Na_2SO_4$. The ether is removed in vacuo to yield 1-[3,3-di(bromomethyl)propyl]-1-methoxymethylbenzene.

The residue is then reacted with 2.4 g of dry magnesium turnings in 300 ml of dry ether under nitrogen at $-10°$ C. Dry $CO_2$ is then bubbled through the solution until no more is absorbed. The solution is neutralized with 25% aqueous $H_2SO_4$, extracted with ether, and dried over $Na_2SO_4$. The ether is removed under vacuum, and the residue esterified with 1 ml $H_2SO_4$ and 100 ml of ethanol. The solution is neutralized, extracted with ether, dried over $Na_2SO_4$, and the solvent removed under reduced pressure to yield 1-[3,3-di(carboxymethyl)propyl]-1-methoxymethylbenzene ($p=1$).

PREPARATION 8

(Preparation of Acetoacetate Derivatives, 5)

(A) A solution of 24 g (0.95 mol) of 4-(2,2-dimethyl-1,3-dioxolan-4-yl)methoxyphenylethan-2-ol (4) in 50 ml of dimethoxyethane and 1 ml of triethylamine was heated to reflux temperature and 8.0 ml of diketene was added dropwise. After the addition was complete the solution was heated at reflux for 2 h. The solvents were removed in vacuo and the residue partitioned between water and ether. The ether was dried over $Na_2SO_4$ and evaporated to a residue which was purified by medium pressure chromatography on silica gel (50% ether-hexane) to afford 25 g of 4-(2,2-dimethyl-1,3-dioxolan-4-yl)-methoxyphenylethylacetoacetate (5) as a colorless oil.

(B) Similarly, by following the procedure of part (A) above, but substituting the compounds prepared in Preparations 5 and 6 for 4-(2,2-dimethyl-1,3-dioxolan-4-yl)methoxyphenylethan-2-ol, the following compounds are prepared:

4-[2-(2,2-dimethyl-1,3-dioxolan-4-yl)ethoxy]phenylethylacetoacetate;

4-[3-(2,2-dimethyl-1,3-dioxolan-4-yl)propyloxy]-phenylethylacetoacetate;

4-(2,2-dimethyl-5-benzyloxymethyl-1,3-dioxolan-4-yl)-methoxyphenylethylacetoacetate;

4-(2-benzyloxyethoxy)phenylethylacetoacetate;

4-(3-benzyloxypropoxy)phenylethylacetoacetate;

4-(1,3-dibenzyloxypropyl-2-oxy)phenylethylacetoacetate;

4-(2,2-dimethyl-1,3-dioxan-5-ylmethoxy)phenylethylacetoacetate;

4-(2,2-dimethyl-1,3-dioxolan-4-yl)methylaminophenylethylacetoacetate;

4-[2-(2,2-dimethyl-1,3-dioxolan-4-yl)ethylamino]-phenylethylacetoacetate;

4-[3-(2,2-dimethyl-1,3-dioxolan-4-yl)propylamino]-phenylethylacetoacetate;

4-(2,2-dimethyl-5-benzyloxymethyl-1,3-dioxolan-4-yl)-methylaminophenylethylacetoacetate;

4-(2-benzyloxyethylamino)phenylethylacetoacetate;

4-(3-benzyloxypropylamino)phenylethylacetoacetate;

4-(2,2-dimethyl-1,3-dioxolan-4-yl)methylthiophenylethylacetoacetate;

4-(2-benzyloxyethylthio)phenylethylacetoacetate;

3-[4-(2,2-dimethyl-1,3-dioxolan-4-yl)methoxyphenyl]-propylacetoacetate;

4-[4-(2,2-dimethyl-1,3-dioxolan-4-yl)methoxyphenyl]-butylacetoacetate;

4-(2,2-dimethyl-1,3-dioxolan-4-yl)methylsulfinylphenylethylacetoacetate;

4-(2-benzyloxyethylsulfinyl)phenylethylacetoacetate;

4-(2,2-dimethyl-1,3-dioxolan-4-yl)methylsulfonylphenylethylacetoacetate;

4-(2-benzyloxyethylsulfonyl)phenylethylacetoacetate;

4-[3,3-di(ethoxycarbonyl)propyl]benzylacetoacetate;

4-[3,3-di(ethoxycarbonyl)ethyl]benzylacetoacetate;

4-[3,3-di(ethoxycarbonyl)ethyl]phenylethylacetoacetate;

4-[3,3-di(ethoxycarbonyl)propyl]phenylethylacetoacetate;

4-[3,3,3-tri(ethoxycarbonyl)propyl]phenylethylacetoacetate.

PREPARATION 9

(Preparation of Compounds of Formula 6)

(A) A solution of 13.2 g (0.039 mol) of 4-(2,2-dimethyl-1,3-dioxolan-4-yl)methoxyphenylethylacetoacetate (5), 4.7 g (0.41 mol) of methyl β-aminocrotonate, and 6.2 g (0.41 mol) of 3-nitrobenzaldehyde in 80 ml of ethanol was heated at reflux for 12 h. Solvent was removed in vacuo and the residue purified by medium pressure chromatography on silica gel (80% ether-hexane) to give 21 g of 2,6-dimethyl-3-methoxycarbonyl-4-(3-nitrophenyl)-5-(2-[4-(2,2-dimethyl-1,3-dioxolan-4-yl)-methoxyphenyl]ethoxycarbonyl)-1,4-dihydropyridine (6) as an orange oil.

(B) Similarly, by following the procedure of part (A) above, but substituting the compounds prepared in Preparation 8 for 4-(2,2-dimethyl-1,3-dioxolan-4-yl)-methoxyphenylethylacetoacetate, the following compounds are prepared:

2,6-dimethyl-3-methoxycarbonyl-4-(3-nitrophenyl)-5-(2-[4-(2,2-dimethyl-1,3-dioxolan-4-yl)ethoxyphenyl]ethoxycarbonyl)-1,4-dihydropyridine;

2,6-dimethyl-3-methoxycarbonyl-4-(3-nitrophenyl)-5-[2-(4-[3-(2,2-dimethyl-1,3-dioxolan-4-yl)propoxy]-phenyl)ethoxycarbonyl]-1,4-dihydropyridine;

2,6-dimethyl-3-methoxycarbonyl-4-(3-nitrophenyl)-5-(2-[4-(2,2-dimethyl-5-benzyloxymethyl-1,3-dioxolan-4-yl)-methoxyphenyl]ethoxycarbonyl)-1,4-dihydropyridine;

2,6-dimethyl-3-methoxycarbonyl-4-(3-nitrophenyl)-5-(2-[4-(2-benzyloxyethoxy)phenyl]ethoxycarbonyl)-1,4-dihydropyridine;

2,6-dimethyl-3-methoxycarbonyl-4-(3-nitrophenyl)-5-(2-[4-(3-benzyloxypropoxy)phenyl]ethoxycarbonyl)-1,4-dihydropyridine;

2,6-dimethyl-3-methoxycarbonyl-4-(3-nitrophenyl)-5-(2-[4-(1,3-dibenzyloxypropyl-2-oxy)phenyl]ethoxycarbonyl)-1,4-dihydropyridine;

2,6-dimethyl-3-methoxycarbonyl-4-(3-nitrophenyl)-5-(2-[4-(2,2-dimethyl-1,3-dioxan-5-ylmethyl)phenyl]ethoxycarbonyl)-1,4-dihydropyridine;

2,6-dimethyl-3-methoxycarbonyl-4-(3-nitrophenyl)-5-(2-[4-(2,2-dimethyl-1,3-dioxolan-4-yl)methylaminophenyl]-ethoxycarbonyl)-1,4-dihydropyridine;

2,6-dimethyl-3-methoxycarbonyl-4-(3-nitrophenyl)-5-[2-(4-[2-(2,2-dimethyl-1,3-dioxolan-4-yl)ethylamino]-phenyl)-ethoxycarbonyl]-1,4-dihydropyridine;

2,6-dimethyl-3-methoxycarbonyl-4-(3-nitrophenyl)-5-[2-(4-[3-(2,2-dimethyl-1,3-dioxolan-4-yl)propylamino]phenyl)-ethoxycarbonyl]-1,4-dihydropyridine;

2,6-dimethyl-3-methoxycarbonyl-4-(3-nitrophenyl)-5-(2-[4-(2,2-dimethyl-5-benzyloxymethyl-1,3-dioxolan-4-yl)-methylaminophenyl]ethoxycarbonyl)-1,4-dihydropyridine;

2,6-dimethyl-3-methoxycarbonyl-4-(3-nitrophenyl)-5-[4-(2-benzyloxyethylamino)phenyl]ethoxycarbonyl-1,4-dihydropyridine;

2,6-dimethyl-3-methoxycarbonyl-4-(3-nitrophenyl)-5-[4-(3-benzyloxypropylamino)phenyl]ethoxycarbonyl-1,4-dihydropyridine;

2,6-dimethyl-3-methoxycarbonyl-4-(3-nitrophenyl)-5-[4-(2,2-dimethyl-1,3-dioxolan-4-yl)methylthiophenyl]ethoxycarbonyl-1,4-dihydropyridine;

2,6-dimethyl-3-methoxycarbonyl-4-(3-nitrophenyl)-5-[4-(2-benzyloxyethylthio)phenyl]ethoxycarbonyl-1,4-dihydropyridine;

2,6-dimethyl-3-methoxycarbonyl-4-(3-nitrophenyl)-5-(3-[4-(2,2-dimethyl-1,3-dioxolan-4-yl)methoxyphenyl]propoxycarbonyl)-1,4-dihydropyridine;

2,6-dimethyl-3-methoxycarbonyl-4-(3-nitrophenyl)-5-(4-[4-(2,2-dimethyl-1,3-dioxolan-4-yl)methoxyphenyl]butoxycarbonyl)-1,4-dihydropyridine;

2,6-dimethyl-3-methoxycarbonyl-4-(3-nitrophenyl)-5-(2-[4-(2,2-dimethyl-1,3-dioxan-5-yl)oxymethylphenyl]ethoxycarbonyl)-1,4-dihydropyridine;

2,6-dimethyl-3-methoxycarbonyl-4-(3-nitrophenyl)-5-(2-[4-(2,2-dimethyl-1,3-dioxolan-4-yl)methylsulfinylphenyl]-ethoxycarbonyl)-1,4-dihydropyridine;

2,6-dimethyl-3-methoxycarbonyl-4-(3-nitrophenyl)-5-(2-[4-(2-benzyloxyethylsulfinyl)phenyl]ethoxycarbonyl)-1,4-dihydropyridine;

2,6-dimethyl-3-methoxycarbonyl-4-(3-nitrophenyl)-5-(2-[4-(2,2-dimethyl-1,3-dioxolan-4-yl)methylsulfonylphenyl]-ethoxycarbonyl)-1,4-dihydropyridine;

2,6-dimethyl-3-methoxycarbonyl-4-(3-nitrophenyl)-5-(2-[4-(2-benzyloxyethylsulfonyl)phenyl]ethoxycarbonyl)-1,4-dihydropyridine;

2,6-dimethyl-3-methoxycarbonyl-4-(3-nitrophenyl)-5-(4-[3,3-di(ethoxycarbonyl)propyl]phenyl)methoxycarbonyl-1,4-dihydropyridine;

2,6-dimethyl-3-methoxycarbonyl-4-(3-nitrophenyl)-5-(4-[3,3-di(ethoxycarbonyl)ethyl]phenyl)methoxycarbonyl-1,4-dihydropyridine;

2,6-dimethyl-3-methoxycarbonyl-4-(3-nitrophenyl)-5-[2-(4-[3,3-di(ethoxycarbonyl)ethyl]phenylethyl)ethoxycarbonyl]-1,4-dihydropyridine;

2,6-dimethyl-3-methoxycarbonyl-4-(3-nitrophenyl)-5-[2-(4-[3,3-di(ethoxycarbonyl)propyl]phenylethyl)ethoxycarbonyl]-1,4-dihydropyridine;

2,6-dimethyl-3-methoxycarbonyl-4-(3-nitrophenyl)-5-[2-(4-[3,3,3-tri(ethoxycarbonyl)propyl]phenylethyl)ethoxycarbonyl]-1,4-dihydropyridine.

PREPARATION 10

(Preparation of 7; Scheme 3)

(A) Benzyl ethers may conveniently be used to protect —YH groups. For example, methyl 4-hydroxyphenylacetate (0.2 mol) is heated at reflux with 25 g benzyl chloride (0.2 mol) and 25 g $K_2CO_3$ (0.2 mol) in 100 ml ethanol. The product is added to dilute aqueous HCl, extracted with ether, and purified by silica gel chromatography to yield methyl 4-benzyloxyphenylacetate (7).

(B) Similarly, proceeding as in part A above but substituting methyl 4-hydroxybenzoate, methyl 4-mercaptophenylacetate, and methyl 3-(4-hydroxyphenyl)propionate for methyl 4-hydroxyphenylacetate, the following compounds are prepared:
methyl 4-benzyloxybenzoate;
methyl 3-(4-benzyloxy)propionate;
methyl 4-benzylthiophenylacetate.

PREPARATION 11

(Preparation of 8)

(A) A solution of 14.0 g of methyl 4-benzyloxyphenylacetate (7) in THF was slowly added with stirring to a solution of 2.0 g LAH in 500 ml of THF. The mixture was heated at reflux 1 h, cooled with ice, then treated sequentially with 2 ml water, 2 ml 15% NaOH, and 4 ml of water. The mixture was filtered and the filtrate evaporated to yield 10 g of crystalline 1-benzyloxy-4-(2-hydroxyethyl)benzene (8), m.p. 84°–85° C.

(B) Similarly, proceeding as in part A above, but substituting the compounds prepared in Preparation 10(B) for methyl 4-benzyloxyphenylacetate, the following compounds were prepared:
1-benzyloxy-4-hydroxymethylbenzene;
1-benzyloxy-4-(3-hydroxypropyl)benzene;
1-benzythio-4-(2-hydroxyethyl)benzene.

(C) Alternatively, for compounds in which Y is —NH or —$NR_2$, one may begin with a hydroxyalkylaniline, protecting the amino group by reaction with di-t-butyldicarbonate. For example, 25 g of 4-(2-hydroxyethyl)aniline and 39.6 g of di-t-butyldicarbonate in 250 ml of THF was heated at reflux for 30 min. The solvent was evaporated and the residue dissolved in ether. The solution was washed with 5% HCl, water, and brine, and dried over $Na_2SO_4$. Evaporation and recrystallization from ethyl acetate-hexane yielded 25 g of N-(t-butoxycarbonyl)-4-(2-hydroxyethyl)aniline (8), m.p. 104°–105° C.

PREPARATION 12

(Preparation of Compounds of Formula 9)

(A) A solution of 4.9 g of 1-benzyloxy-4-(2-hydroxyethyl)benzene (8) in 100 ml of dimethoxyethane (DME) and 5 drops triethylamine was heated to reflux and 1.8 ml of diketene was slowly added. The solvent was removed under reduced pressure to yield 6.4 g of 2-(benzyloxyphenyl)ethylacetoacetate (9), m.p. 54°–56° C.

(B) Similarly, proceeding as in part A above but substituting the compounds prepared in Preparation 11(B-C) above for 1-benzyloxy-4-(2-hydroxyethyl)benzene, the following compounds are prepared:
(4-benzyloxy)benzyl acetoacetate;
3-(4-benzyloxyphenyl)propylacetoacetate;
2-(4-benzylthiophenyl)ethylacetoacetate;
2-[4-(t-butoxycarbonylamino)phenyl]ethylacetoacetate.

PREPARATION 13

(Preparation of Compounds of Formula 10; Deprotection)

(A) A solution of 6.2 g of 2-(4-benzyloxyphenyl)-ethylacetoacetate in 100 ml of ethanol with 0.5 g of 10% palladium on carbon was hydrogenated at 50 psi for 18 h. The mixture was filtered and the filtrate evaporated to afford 4.3 g of 2-(4-hydroxyphenyl)ethylacetoacetate.

(B) Similarly, proceeding as in part (A) above but substituting the benzyloxy and benzylthio compounds prepared in Preparation 12(B) for 2-(4-benzyloxyphenyl)-ethylacetoacetate, the following compounds are prepared:
4-hydroxybenzylacetoacetate;
3-(4-hydroxyphenyl)propylaceotacetate;
2-(4-mercaptophenyl)ethylacetoacetate.

PREPARATION 14

(Preparation of Compounds of Formula 11)

(A) A mixture of 4.3 g of 2-(4-hydroxyphenyl)-ethylacetoacetate (10), 2.3 g of methyl β-aminocrotonate, 2.9 g of 3-nitrobenzaldehyde and 70 ml of methanol was heated at reflux for 12 hours. The solvent was removed under reduced pressure and the residue purified by silica gel chromatography using 50:50 ethyl acetate-hexane to yield 5.9 g of 2,6-dimethyl-3-methoxycarbonyl-4-(3-nitrophenyl)-5-[2-(4-hydroxyphenyl)ethoxycarbonyl]-1,4-dihydropyridine (11), as an amorphous solid. Calculated for $C_{24}H_{24}N_2O_7 \cdot 1.5H_2O$: C-60.12, H-5.68, N-5.84. Found: C-60.55, H-5.33, N-6.03.

(B) Similarly, proceeding as in part (A) above but substituting the compounds prepared in Preparation 13(B) for 2-(4-hydroxyphenyl)ethylacetoacetate, the following compounds are prepared:

1,6-dimethyl-3-methoxycarbonyl-4-(3-nitrophenyl)-5-(4-hydroxy)benzyloxycarbonyl;-1,4-dihydropyridine;

2,6-dimethyl-3-methoxycarbonyl—(3-nitrophenyl)-5-[3-(4-hydroxyphenyl)propyloxycarbonyl]-1,4-dihydropyridine;

2,6-dimethyl-3-methoxycarbonyl-4-(3-nitrophenyl)-5-[2-(4-mercaptophenyl)ethoxycarbonyl]-1,4-dihydropyridine.

(C) Similarly, 30 g of 2-[4-(t-butoxycarbonylamino)phenyl]ethylacetate (9), 11.5 g of methyl β-aminocrotonate, and 15.1 g of 3-nitrobenzaldehyde in 200 ml of ethanol was heated at reflux for 12 h. The solvent was removed under reduced pressure and the residue of crude 1,6-dimethyl-3-methoxycarbonyl-4-(3-nitrophenyl)-5-[2-(4-t-butoxycarbonylaminophenyl)ethoxycarbonyl]-1,4-dihydropyridine dissolved in 100 ml of dichloromethane and 100 ml of formic acid. The mixture was heated on a steam bath for 20 min., followed by solvent removal under reduced pressure. The residue was partitioned between 5% aqueous HCl and ethyl acetate, and the aqueous layer basified with NaOH and extracted with ether. The ether was dried and evaporated, and the residue crystallized from ethyl acetate-hexane to afford 20.4 g of 2,6-dimethyl-3-methoxycarbonyl-4-(3-nitrophenyl)-5-[2-(4-aminophenyl)ethoxycarbonyl]-1,4-dihydropyridine (11), m.p. 107°-109° C. Calculated for $C_{24}H_{25}N_3O_6$: C-63.84, H-5.59, N-9.31. Found: C-63.99, H-5.69, N-9.13.

(D) Similarly, proceeding as in part (A) above but substituting 3-trifluoromethylbenzaldehyde, the following compounds are prepared:

2,6-dimethyl-3-methoxycarbonyl-4-(3-trifluoromethylphenyl)-5-[2-(4-hydroxyphenyl)ethoxycarbonyl]-1,4-dihydropyridine;

2,6-dimethyl-3-methoxycarbonyl-4-(2-chlorophenyl)-5-[2-(4-hydroxyphenyl)ethoxycarbonyl]-1,4-dihydropyridine.

(E) Similarly, proceeding as in part (A) above but substituting propyl β-aminocrotonate or methoxyethyl β-aminocrotonate for methyl β-aminocrotonate, the following compounds are prepared:

2,6-dimethyl-3-propyloxycarbonyl-4-(3-nitrophenyl)-5-[2-(4-hydroxyphenyl)ethoxycarbonyl]-1,4-dihydropyridine;

2,6-dimethyl-3-methoxyethoxycarbonyl-4-(3-nitrophenyl)-5-[2-(4-hydroxyphenyl)ethoxycarbonyl]-1,4-dihydropyridine.

EXAMPLE 1

(Preparation of Compounds of Formula 1 via Scheme 1)

(A) A solution of 21 g of 2,6-dimethyl-3-methoxycarbonyl-4-(3-nitrophenyl)-5-(2-[4-(2,2-dimethyl-1,3-dioxolan-4-yl)methoxyphenyl]ethoxycarbonyl)-1,4-dihydropyridine (6) in 150 ml of acetone and 50 ml of water was treated with 10 ml of hydrochloric acid and the mixture heated at reflux for 6 h. Water (500 ml) was added and the mixture was extracted with ether. The ether layer was dried over $Na_2SO_4$ and evaporated to an oil which was purified by medium pressure chromatography on silica gel (90% ethyl acetate-hexane) to give 12 g of 2,6-dimethyl-3-methoxycarbonyl-4-(3-nitrophenyl)-5-(2-[4-(2,3-dihydroxypropoxy)phenyl]ethoxycarbonyl)-1,4-dihydropyridine (1) as a thick oil which crystallized upon trituration with ethyl acetate, m.p. 117°-118° C. Calculated for $C_{27}H_{30}N_2O_9$: C-61.59, H-5.74, N-5.32. Found: C-61.42, H-5.76, N-5.31.

(B) Similarly, by following the procedure of part (A) above, but substituting the compounds prepared in Preparation 9 for 2,6-dimethyl-3-methoxycarbonyl-4-(3-nitrophenyl)-5-(2-[4-(2,2-dimethyl-1,3-dioxolan-4-yl)-methoxyphenyl]ethoxycarbonyl)-1,4-dihydropyridine (6), the following compounds are prepared:

2,6-dimethyl-3-methoxycarbonyl-4-(3-nitrophenyl)-5-(2-[4-(3,4-dihydroxybutoxy)phenyl]ethoxycarbonyl)-1,4-dihydropyridine;

2,6-dimethyl-3-methoxycarbonyl-4-(3-nitrophenyl)-5-(2-[4-(4,5-dihydroxypentyloxy)phenyl]ethnoxycarbonyl)-1,4-dihydropyridine;

2,6-dimethyl-3-methoxycarbonyl-4-(3-nitrophenyl)-5-(2-[4-(2,3-dihydroxypropylamino)phenyl]ethoxycarbonyl)-1,4-dihydropyridine;

2,6-dimethyl-3-methoxycarbonyl-4-(3-nitrophenyl)-5-(2-[4-(3,4-dihydroxybutylamino)phenyl]ethoxycarbonyl)-1,4-dihydropyridine;

2,6-dimethyl-3-methoxycarbonyl-4-(3-nitrophenyl)-5-(2-[4-(4,5-dihydroxypentylamino)phenyl]ethoxycarbonyl)-1,4-dihydropyridine;

2,6-dimethyl-3-methoxycarbonyl-4-(3-nitrophenyl)-5-(2-[4-(4-benzyloxy-2,3-dihydroxybutylamino)phenyl]ethoxycarbonyl)-1,4-dihydropyridine;

2,6-dimethyl-3-methoxycarbonyl-4-(3-nitrophenyl)-5-(2-[4-(2,3-dihydroxypropylthio)phenyl]ethoxycarbonyl-1,4-dihydropyridine;

2,6-dimethyl-3-methoxycarbonyl-4-(3-nitrophenyl)-5-(3-[4-(2,3-dihydroxypropoxy)phenyl]propoxycarbonyl)-1,4-dihydropyridine;

2,6-dimethyl-3-methoxycarbonyl-4-(3-nitrophenyl)-5-(4-[4-(2,3-dihydroxypropoxy)phenyl]butoxycarbonyl-1,4-dihydropyridine;

2,6-dimethyl-3-methoxycarbonyl-4-(3-nitrophenyl)-5-(2-[4-(2,3-dihydroxypropylsulfinyl)phenyl]ethoxycarbonyl)-1,4-dihydropyridine;

2,6-dimethyl-3-methoxycarbonyl-4-(3-nitrophenyl)-5-(2-[4-(2,3-dihydroxypropylsulfonyl)phenyl]ethoxycarbonyl)-1,4-dihydropyridine;

2,6-dimethyl-3-methoxycarbonyl-4-(3-nitrophenyl)-5-(2-[4-(2,3-dihydroxyprop-2-ylsulfonyl)phenyl]ethoxycarbonyl)-1,4-dihydropyridine.

(C) Compounds of formula 6 which are protected with benzyl ethers may be deprotected as follows:

A solution of 6.2 g of 2,6-dimethyl-3-methoxycarbonyl-4-(3-nitrophenyl)-5-(2-[4-(2-benzyloxyethoxy)-phenyl]ethoxycarbonyl)-1,4-dihydropyridine in 100 ml of ethanol with 0.5 g of 10% palladium on carbon is hydrogenated at 50 psi for 18 h. The mixture is filtered and the filtrate evaporated to afford 2,6-dimethyl-3-methoxycarbonyl-4-(3-nitrophenyl)-5-(2-[4-(2-hydroxyethoxy)phenyl]ethoxycarbonyl)-1,4-dihydropyridine.

(D) Similarly, proceeding as in part (C) above but substituting the benzyloxy compounds prepared in Preparation 9 and part (B) above for 2,6-dimethyl-3-methoxycarbonyl-4-(3-nitrophenyl)-5-(2-[4-(2-benzyloxyethoxy)phenyl]ethoxycarbonyl)-1,4-dihydropyridine, the following compounds are prepared:

2,6-dimethyl-3-methoxycarbonyl-4-(3-nitrophenyl)-5-(2-[4-(2,3,4-trihydroxybutoxy)phenyl]ethoxycarbonyl)-1,4-dihydropyridine;

2,6-dimethyl-3-methoxycarbonyl-4-(3-nitrophenyl)-5-(2-[4-(3-hydroxypropoxy)phenyl]ethoxycarbonyl)-1,4-dihydropyridine;

2,6-dimethyl-3-methoxycarbonyl-4-(3-nitrophenyl)-5-(2-[4-(2-hydroxyethylamino)phenyl]ethoxycarbonyl)-1,4-dihydropyridine;

2,6-dimethyl-3-methoxycarbonyl-4-(3-nitrophenyl)-5-(2-[4-(3-hydroxypropylamino)phenyl]ethoxycarbonyl)-1,4-dihydropyridine;

2,6-dimethyl-3-methoxycarbonyl-4-(3-nitrophenyl)-5-(2-[4-(2-hydroxyethylthio)phenyl]ethoxycarbonyl)-1,4-dihydropyridine;

2,6-dimethyl-3-methoxycarbonyl-4-(3-nitrophenyl)-5-(2-[4-(2,3,4-trihydroxybutylamino)phenyl]ethoxycarbonyl)-1,4-dihydropyridine;

2,6-dimethyl-3-methoxycarbonyl-4-(3-nitrophenyl)-5-(2-[4-(2-hydroxyethylsulfinyl)phenyl]ethoxycarbonyl)-1,4-dihydropyridine;

2,6-dimethyl-3-methoxycarbonyl-4-(3-nitrophenyl)-5-(2-[4-(2-hydroxyethylsulfonyl)phenyl]ethoxycarbonyl)-1,4-dihydropyridine;

EXAMPLE 2

(Preparation of Ethers of Formula 1 via Scheme 3)

(A) A mixture of 1.0 g of 2,6-dimethyl-3-methoxycarbonyl-4-(3-nitrophenyl)-5-[2-(4-hydroxyphenyl)ethoxycarbonyl]-1,4-dihydropyridine (11), 0.5 g of $K_2CO_3$, and 0.5 g of ethylene carbonate in 20 ml of toluene was heated at reflux for 18 h. The mixture was filtered and the filtrate evaporated to yield 1.0 g of 2,6-dimethyl-3-methoxycarbonyl-4-(3-nitrophenyl)-5-(2-[4-(2-hydroxyethoxy)phenyl]ethoxycarbonyl)-1,4-dihydropyridine (1, $R_1=A_1$, m=2, p=0) as an amorphous solid.

Calculated for $C_{26}H_{28}N_2O_8$: C-62.89, H-5.68, N-5.64. Found: C-62.73, H-5.73, N-5.59.

(B) Similarly, proceeding as in part (A) above but substituting the compounds prepared in Preparation 14 (B-E), the following compounds are obtained:

2,6-dimethyl-3-methoxycarbonyl-4-(3-nitrophenyl)-5-[4-(2-hydroxyethoxy)benzyl]oxycarbonyl-1,4-dihydropyridine;

2,6-dimethyl-3-methoxycarbonyl-4-(3-nitrophenyl)-5-[2-(4-hydroxyethylaminophenyl)ethoxycarbonyl]-1,4-dihydropyridine;

2,6-dimethyl-3-methoxycarbonyl-4-(3-trifluoromethylphenyl)-5-[2-(4-hydroxyethoxyphenyl)ethoxycarbonyl]-1,4-dihydropyridine;

2,6-dimethyl-3-methoxycarbonyl-4-(2-chlorophenyl)-5-[2-(4-hydroxyethoxyphenyl)ethoxycarbonyl]-1,4-dihydropyridine;

2,6-dimethyl-3-propyloxycarbonyl-4-(3-nitrophenyl)-5-[2-(4-hydroxyethoxyphenyl)ethoxycarbonyl]-1,4-dihydropyridine;

2,6-dimethyl-3-methoxyethoxycarbonyl-4-(3-nitrophenyl)-5-[2-(4-hydroxyethoxyphenyl)ethoxycarbonyl]-1,4-dihydropyridine.

(C) Similarly, a solution of 4.5 g of 2,6-dimethyl-3-methoxycarbonyl-4-(3-nitrophenyl)-5-[2-(4-aminophenyl)ethoxycarbonyl]-1,4-dihydropyridine (11), 1.8 ml 2-bromoethanol, 2 ml triethylamine and 20 ml DMF was stirred at 80° C. for 3 h. The mixture was added to water and extracted with ethyl acetate. The ethyl acetate was washed with water, dried over $Na_2SO_4$, evaporated to a residue, and purified by silica gel chromatography with 75% ethyl acetate-hexane to afford 2,6-dimethyl-3-methoxycarbonyl-4-(3-nitrophenyl)-5-(2-[4-(2-hydroxyethylamino)phenyl]ethoxycarbonyl)-1,4-dihydropyridine (1) as a free base. This was dissolved in methanolic HCl and evaporated under reduced pressure to yield 2.6 g of 2,6-dimethyl-3-methoxycarbonyl-4-(3-nitrophenyl)-5-(2-[4-(2-hydroxyethylamino)phenyl]ethoxycarbonyl)-1,4-dihydropyridine hydrochloride as an amorphous solid, m.p. 102°–104° C. Calculated for $C_{26}H_{30}ClN_3O_7$: C-58.70, H-5.68, N-7.90. Found: C-58.50, H-5.72, N-7.80.

(D) Similarly, proceeding as in part (C) above but substituting 3 g of 2,6-dimethyl-3-methoxycarbonyl-4-(3-nitrophenyl)-5-[2-(4-aminophenyl)ethoxycarbonyl]-1,4-dihydropyridine (11) for 4.5 g, 2 ml of 2-bromoethanol for 1.8 ml, and stirring at 90° C. for 48 h rather than 80° C. for 3 h, yields 2 g of the salt 2,6-dimethyl-3-methoxycarbonyl-4-(3-nitrophenyl)-5-(2-[4-di(2-hydroxyethyl)aminophenyl]ethoxycarbonyl)-1,4-dihydropyridine hydrochloride (1) m.p. 90°–92° C. Calculated for $C_{28}H_{34}ClN_3O_8$: C-58.38, H-5.95, N-7.29. Found: C-58.36, H-5.91, N-7.03.

EXAMPLE 3

(Preparation of Esters of Formula 1 via Scheme 3)

(A) A mixture of 2 g of 2,6-dimethyl-3-methoxycarbonyl-4-(3-nitrophenyl)-5-[2-(4-hydroxyphenyl)ethoxycarbonyl]-1,4-dihydropyridine (11), 1.3 g of $K_2CO_3$, and 1 ml of methyl bromoacetate in 100 ml of acetone was heated at reflux for 18 h. The mixture was filtered and the filtrate evaporated to an oil. The oil was triturated with hexane to yield 2,6-dimethyl-3-methoxycarbonyl-4-(3-nitrophenyl)-5-[2-(4-methoxycarbonylmethoxyphenyl)-ethoxycarbonyl]-1,4-dihydropyridine (1) as an amorphous solid. Calculated for $C_{27}H_{28}N_2O_9$: C-60.93, H-5.51, N-5.47. Found: C-61.06, H-5.52, N-5.42.

(B) Similarly, proceeding as in part A above but substituting the compounds prepared in Preparation 14 (B, D, E) for 2,6-dimethyl-3-methoxycarbonyl-4-(3-nitrophenyl)-5-[2-(4-hydroxyphenyl)ethoxycarbonyl]-1,4-dihydropyridine, the following compounds are prepared:

2,6-dimethyl-3-methoxycarbonyl-4-(3-nitrophenyl)-5-(4-methoxycarbonylmethoxy)benzyloxycarbonyl-1,4-dihydropyridine;

2,6-dimethyl-3-methoxycarbonyl-4-(3-nitrophenyl)-5-[3-(4-methoxycarbonylmethoxyphenyl)propoxycarbonyl]-1,4-dihydropyridine;

2,6-dimethyl-3-methoxycarbonyl-4-(3-nitrophenyl)-5-[2-(4-methoxycarbonylmethylthiophenyl)ethoxycarbonyl]-1,4-dihydropyridine;

2,6-dimethyl-3-methoxycarbonyl-4-(3-nitrophenyl)-5-[2-(4-methoxycarbonylmethylaminophenyl)ethoxycarbonyl]-1,4-dihydropyridine;

2,6-dimethyl-3-methoxycarbonyl-4-(3-trifluoromethylphenyl)ethoxycarbonyl]-1,4-dihydropyridine;

2,6-dimethyl-3-methoxycarbonyl-4-(2-chlorophenyl)-5-[2-(4-methoxycarbonylmethoxyphenyl)ethoxycarbonyl]-1,4-dihydropyridine;

2,6-dimethyl-3-propyloxycarbonyl-4-(3-nitrophenyl)-5-[2-(4-methoxycarbonylmethoxyphenyl)ethoxycarbonyl]-1,4-dihydropyridine;

2,6-dimethyl-3-methoxycarbonyl-4-(3-nitrophenyl)-5-[2-(4-methoxycarbonylmethoxyphenyl)ethoxycarbonyl]-1,4-dihydropyridine.

EXAMPLE 4

(Conversion of Esters to Acids)

(A) A solution of 0.5 g of 2,6-dimethyl-3-methoxycarbonyl-4-(3-nitrophenyl)-5-[2-(4-methoxycarbonylmethoxyphenyl)ethoxycarbonyl]-1,4-dihydropyridine, 0.5 ml 10% aqueous NaOH, and 20 ml of methanol was heated on a steam bath for 20 min. The mixture was diluted with water, acidified with HCl, and extracted with ethyl acetate. The ethyl acetate was dried and evaporated to yield 0.40 g of 2,6-dimethyl-3-methoxycarbonyl-4-(3-nitrophenyl)-5-[2-(4-carboxymethylphenyl)ethoxycarbonyl]-1,4-dihydropyridine (1). Calculated for $C_{26}H_{26}N_2O_9 \cdot 0.5H_2O$: C-59.17, H-5.36, N-5.52.

Found: C-59.41, H-5.42, N-5.31.

(B) Similarly, proceeding as in part A above but substituting the compounds prepared in Example 3(B), the following compounds are prepared:

2,6-dimethyl-3-methoxycarbonyl-4-(3-nitrophenyl)-5-[4-carboxymethoxy)benzyloxycarbonyl]-1,4-dihydropyridine;

2,6-dimethyl-3-methoxycarbonyl-4-(3-nitrophenyl)-5-[3-(4-carboxymethoxyphenyl)propoxycarbonyl]-1,4-dihydropyridine;

2,6-dimethyl-3-methoxycarbonyl-4-(3-nitrophenyl)-5-[2-(4-carboxymethylthiophenyl)ethoxycarbonyl]-1,4-dihydropyridine;

2,6-dimethyl-3-methoxycarbonyl-4-(3-nitrophenyl)-5-[2-(4-carboxymethylaminophenyl)ethoxycarbonyl]-1,4-dihydropyridine;

2,6-dimethyl-3-methoxycarbonyl-4-(3-trifluoromethylphenyl)ethoxycarbonyl]-1,4-dihydropyridine;

2,6-dimethyl-3-methoxycarbonyl-4-(2-chlorophenyl)-5-2-(4-carboxymethoxyphenyl)ethoxycarbonyl]-1,4-dihydropyridine;

2,6-dimethyl-3-propyloxycarbonyl-4-(3-nitrophenyl)-5-[2-(4-carboxymethoxyphenyl)ethoxycarbonyl]-1,4-dihydropyridine;

2,6-dimethyl-3-methoxycarbonyl-4-(3-nitrophenyl)-5-[2-(4-carboxymethoxyphenyl)ethoxycarbonyl]-1,4-dihydropyridine.

EXAMPLE 5

(Preparation of Salts From Free Bases)

8.0 g of 2,6-dimethyl-3-methoxycarbonyl-4-(3-nitrophenyl)-5-[2-(4-methoxycarbonylmethylaminophenyl)ethoxycarbonyl]-1,4-dihydropyridine is dissolved in methanol and acidified with methanolic HCl. The precipitate is washed with $Et_2O$ to give 7.0 g of the hydrochloride salt of 2,6-dimethyl-3-methoxycarbonyl-4-(3-nitrophenyl)-5-[2-(4-methoxycarbonylmethylaminophenyl)ethoxycarbonyl]-1,4-dihydropyridine.

In a similar manner, all compounds of formula 1 in base form prepared in accordance with the methods described above can be converted to their pharmaceutically acceptable acid addition salts by treatment with the appropriate acid, for example, hydrobromic acid, sulfuric acid, nitric acid, phosphoric acid, acetic acid, propionic acid, glycolic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid and the like.

EXAMPLE 6

(Preparation of Free Bases From Salts)

A solution of 3.5 g of 2,6-dimethyl-3-methoxycarbonyl-4-(3-nitrophenyl)-5-[2-(4-methoxycarbonylmethylaminophenyl)ethoxycarbonyl]-1,4-dihydropyridine hydrochloride salt in water (50 ml) is adjusted to pH 12 with $NH_4OH$ solution and extracted with methylene chloride. The methylene chloride is then evaporated to afford 3 g of 2,6-dimethyl-3-methoxycarbonyl-4-(3-nitrophenyl)-5-[2-(4-methoxycarbonylmethylaminophenyl)ethoxycarbonyl]-1,4-dihydropyridine as the free base.

In a similar manner, all acid addition salts of compounds of formula 1 prepared in accordance with the methods described above can be converted to their free base form.

EXAMPLE 7

(Formulations)

The following example illustrates the preparation of representative pharmaceutical formulations containing an active compound of formula 1, e.g., 2,6-dimethyl-3-methoxycarbonyl-4-(3-nitrophenyl)-5-(2-[4-(2,3-dihydroxypropoxy)phenyl]ethoxycarbonyl)-1,4-dihydropyridine (1).

| I.V. Formulation | | |
|---|---|---|
| Active compound | 0.01 | g |
| Propylene glycol | 20. | g |
| Polyethylene glycol 400 | 20. | g |
| Tween 80 | 1. | g |
| 0.9% Saline solution qs | 100. | ml |

The active compound is dissolved in propylene glycol, polyethylene glycol 400 and Tween 80. A sufficient quantity of 0.9% saline solution is then added with stirring to provide 100 ml of the I.V. solution which is filtered through a 0.2 micron membrane filter and packaged under sterile conditions.

| TABLET FORMULATION | parts by weight |
|---|---|
| Active compound | 5.0 |
| Magnesium stearate | 0.75 |
| Starch | 0.75 |
| Lactose | 29.0 |
| PVP (polyvinylpyrrolidone) | 0.75 |

The above ingredients are combined and granulated using methanol as the solvent. The formulation is then dried and formed into tablets (containing 2 mg of active compound) with an appropriate tabletting machine.

EXAMPLE 8

(Spontaneously Hypertensive Rat Assay)

Twenty-four previously trained adult male spontaneously hypertensive rats were distributed into 6 groups (4 animals per group) with approximately equal mean systolic blood pressures. The 6 groups were then studied concurrently in a 2-day compound screening procedure.

Test compounds were randomly assigned to each group. Five groups received potential antihypertensive agents and 1 control group received vehicle only (water and Tween).

At approximately 17 hours prior to the first day of dosing food was removed from the rat cages. On the morning of Day 1, a group of 4 rats was orally dosed (by gavage) with 12.5 mg/kg or 25 mg/kg of a compound of formula 1 dissolved/suspended in water (using 2-3 drops Tween 80) with a homogenizer at concentrations such that 0.1 ml of solution was administered per 10 g of body weight. At 4½ hours post dose, food was put back in the cages and the rats were allowed to eat for 2½ hours, after which food was again removed. On the morning of Day 2, rats were orally dosed as described above. Immediately after dosing, the rats were put in restrainers and placed in a heated chamber (30±1.0° C.) for four hours. Normal feeding resumed at the end of the study on Day 2.

Systolic blood pressure (i.e., pressure at the appearance of the first pulse) were recorded using photoelectric transducers. The coccygeal arteries of 3 rats (in a horizontal group) were simultaneously occluded by pump-inflated tail cuffs that were automatically inflated to 300 mmHg and then deflated. A pressure curve and tail pulses were simultaneously monitored on an MFE recorder. Four consecutive (at 30 second intervals) traces were recorded for each rat in a given horizontal group at one, two, three and four hours post compound administration. Subsequent horizontal groups were automatically tested in the same manner.

The mean systolic blood pressure (SBP) of each rat at each observation time was calculated. The SBP of the animals in each dose group were compared to the SBP of the animals in the control group (vehicle only) at each observation time using a one-way analysis of variance test. A compound exhibiting $p \leq 0.05$ at any observation time was considered to exhibit significant antihypertensive activity. Compounds significantly decreasing blood pressure 20 mmHg or more from control values at all four observation times were considered worthy of further examination. In these instances heart rates were calculated and tested for significant change from control heart rate values using the two-tailed test. Pressures were read at hours 1, 2, 3 and 4 after dosing on both days 1 and 2. The compounds of the invention exhibited positive antihypertensive activity in this test.

EXAMPLE 9

(Canine Echocardiography Assay)

A group of mongrel dogs, 18 to 25 kg, were chosen for the clarity of images that could be obtained from them via ultrasonic two-dimensional echocardiography (2DE). Animals from this group were used in two different models employing 2DE. In the first model the dogs were anesthetized; in the second they were conscious and non-sedated throughout the drug administration.

In both models a small branch of femoral artery was cannulated, via an arterial cutdown, with a length of water-filled tubing connected to a pressure transducer. In the conscious model, the femoral cutdown site was anesthetized with a local subcutaneous injection of 2% Lidocaine. This transducer provided a means to monitor blood pressure. Blood pressure and ECG were recorded on a two channel chart recorder.

An ultrasound realtime scanner, connected to a 3 MgHz endfire transducer, placed in a right parasternal approach on the fourth or fifth intercostal space, produced the 2DE images. Images included a long axis view of the left ventricle defined as simultaneously imaging the apex, mitral valve, and a round left atrium. Additionally, short axis views at the high papillary muscle level were obtained. All images were recorded on video tape for later analysis. Analysis was accomplished using a computerized graphics program interfaced with the videorecorder and a bit pad.

In the first model the dogs were anesthetized with sodium pentobarbital. They were placed on their right sides on a support that allowed access, via a cutout to the right parasternal area. Doses of 50, 100, 200 and 500 µg/kg of a compound of the invention were administered intravenously over the course of the experiment day. The compound was dissolved in 2:1 distilled water-dimethyl acetamide. Control values were obtained for each dose and further measurements were taken at 3, 5, 10, 15, and 30 minutes after administration of each dose.

In the second model the dogs were trained to stand quietly for several hours in a sling. The right parasternal area was accessed via a buttoned-down panel in the sling. Doses of 200 and 250 µg/kg of a compound of the invention were administered intravenously, dissolved in 7:1 distilled water-ethanol, as were doses of 150 and 100 µg/kg of a compound of the invention dissolved in 3:1 distilled water-dimethyl acetamide. Additionally, doses of 5, 2, 1 and 0.75 mg/kg of a compound of the invention were administered orally, with the compound in a gelatin capsule. Control values were obtained prior to each dose. During the intravenous studies additional measurements were obtained at intervals of 5, 10, 15, 30, 45, and 60 minutes after the administration of each dose. During the oral studies additional measurements were obtained at intervals of 10, 20, 30, 45, 60, 75, 90, 105, 120, and 180 minutes after the administration of each dose. The compounds of the invention demonstrate positive activity in this assay.

EXAMPLE 10

(Anesthetized Dog Assay)

Mongrel dogs ranging in weight from 14 to 21 kg were anesthetized with pentobarbital sodium (35 mg/kg, i.v.), intubated and the chest opened at the left fifth intercostal space. The animals were instrumented to measure the following parameters: systolic, diastolic and mean blood pressure, heart rate, left ventricular pressure, left ventricular dp/dt max, pulmonary capillary wedge pressure, central venous pressure, cardiac output, systemic vascular resistance, contractile force, and coronary blood flow.

Left ventricular pressure was measured using a Millar micro-tip catheter. Electronic differentiation of this signal provided dp/dt maximum. Systolic, diastolic and mean blood pressure, and central venous pressure were evaluated using fluid-filled Statham pressure transducers. Cardiac output and pulmonary capillary wedge pressure were measured using a Swan-Ganz catheter connected to a Statham water-filled pressure transducer and a Gould Cardiac Index Computer. Contractile force was determined via a Walton-Brodie Strain gauge arch sewn to the left ventricle. Systemic vascular resistance was calculated using cardiac output and blood pressure measurements. Epicardial coronary blood flow was measured with an electromagnetic flow probe (Carolina Medical Electronics, Co.). Myocardial blood flow was evaluated using radioactive-labelled microspheres (5: $^{85}Sr$, $^{141}Ce$, $^{51}Cr$, $^{113}Sn$, $^{46}Sc$). This data was counted with a Packard model 3500 gamma counter and a Canberra Model Multichannel Analyzer, and analyzed with the aid of Syntex-developed software run on a HP1000 Computer.

A compound of the invention was prepared for administration in a vehicle of dimethylacetamide and saline (for intravenous use) or dimethylacetamide and water (for intraduodenal use). Appropriate controls were also examined.

One group of animals was given a compound of the invention intravenously at the following doses: 25, 50, 100, 200 and 500 μg/kg. The above-named parameters were monitored for at least 30 minutes after each dose.

The second group of animals was given a compound of the invention intraduodenally at a dose of 5 mg/kg. The above mentioned parameters were monitored for 3 to 4 hours after drug administration.

In a third group of animals, a compound of the invention was administered intracoronary to determine the direct local effects of the compound. All of the above-mentioned parameters were monitored for 10-15 minutes after drug administration except myocardial blood flow (microsphere method). The doses administered were 1, 2, 5, 10, and 20 μg/kg.

In a fourth group of animals, a compound of the invention was administered intravenously after pretreatment with d-, l-, or dl-propranolol (0.5 mg/kg, i.v.). All parameters were monitored for one hour after drug administration.

The data was summarized with mean values ± the standard error from the mean. When indicated, statistics were done with paired or unpaired Student's t-test. The compounds of the invention exhibit positive activity in this assay.

What is claimed is:
1. A compound of the formula

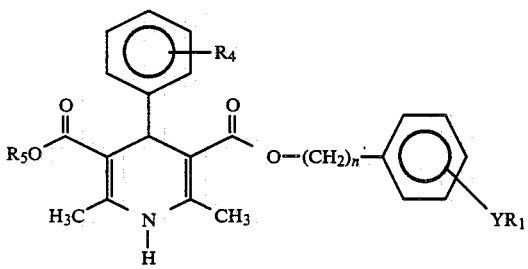

(1)

or a pharmaceutically acceptable acid addition salt thereof, wherein:
n is an integer from 0 to 8;
Y is —O, —NH, —NR$_2$, —S, —S(O), —S(O)$_2$, or a bond;
R$_1$ and R$_2$ are each independently A$_1$, A$_2$, A$_3$ or A$_4$ where
A$_1$ is —(CH$_2$)$_m$(CHOH)$_p$CH$_2$OH;
A$_2$ is —(CH$_2$)$_q$CH$_{(3-r)}$[(CH$_2$)$_s$OH]$_r$;
A$_3$ is —(CH$_2$)$_q$CH$_{(3-r)}$[(CH$_2$)$_p$COOR$_3$]$_r$; and
A$_4$ is —(CH$_2$)$_m$COOR$_3$; where
m is an integer from 1 to 8;
p is an integer from 0 to 4;
q is an integer from 0 to 8;
r is 2 or 3;
s is an integer from 1 to 4; and
R$_3$ is H or alkyl of 1 to 18 carbon atoms;
R$_4$ is —NO$_2$, —CF$_3$, or halo; and
R$_5$ is lower alkyl or —CH$_2$CH$_2$OCH$_3$.

2. The compound of claim 1 wherein R$_4$ is meta nitro.
3. The compound of claim 2 wherein R$_5$ is methyl.
4. The compound of claim 3 wherein Y is para —O and R$_1$ is A$_1$.
5. The compound of claim 4 wherein m is 1 and p is 1.
6. The compound of claim 5 wherein n is 2, i.e., the compound 2,6-dimethyl-3-methoxycarbonyl-4-(3-nitrophenyl)-5-(2-[4-(2,3-dihydroxypropoxy)phenyl]ethoxycarbonyl)-1,4-dihydropyridine.
7. The compound of claim 5 wherein n is 1, i.e., the compound 2,6-dimethyl-3-methoxycarbonyl-4-(3-nitrophenyl)-5-[4-(2,3-dihydroxypropoxy)phenyl]methoxycarbonyl)-1,4-dihydropyridine.
8. The compound of claim 5 wherein n is 3, i.e., the compound 2,6-dimethyl-3-methoxycarbonyl-4-(3-nitrophenyl)-5-(3-[4-(2,3-dihydroxypropoxy)phenyl]propoxycarbonyl)-1,4-dihydropyridine.
9. The compound of claim 3 wherein n is 2, Y is para —O and R$_1$ is A$_2$.
10. The compound of claim 9 wherein q is 0, r is 2, and s is 1, i.e., the compound 2,6-dimethyl-3-methoxycarbonyl-4-(3-nitrophenyl)-5-(2-[4-(1,3-dihydroxyprop-2-oxy)phenyl]ethoxycarbonyl)-1,4-dihydropyridine.
11. The compound of claim 3 wherein n is 2, Y is para —NH and R$_1$ is A$_1$.
12. The compound of claim 11 wherein m is 1, and p is 0, i.e., the compound 2,6-dimethyl-3-methoxycarbonyl-4-(3-nitrophenyl)-5-(2-[4-(2-hydroxyethylamino)phenyl]ethoxycarbonyl)-1,4-dihydropyridine hydrochloride.
13. The compound of claim 3 wherein n is 2, Y is para —NR$_2$, and R$_1$ and R$_2$ are A$_1$.
14. The compound of claim 13 wherein m is 1, and p is 0, i.e, the compound 2,6-dimethyl-3-methoxycarbonyl-4-(3-nitrophenyl)-5-(2-[4-[N,N-bis(2-hydroxyethyl)amino]phenyl]-ethoxycarbonyl)-1,4-dihydropyridine hydrochloride.
15. A method for treating hypertension, congestive heart failure, angina, migraine, and vasospastic disorders which comprises administering a therapeutically effective amount of a compound of formula

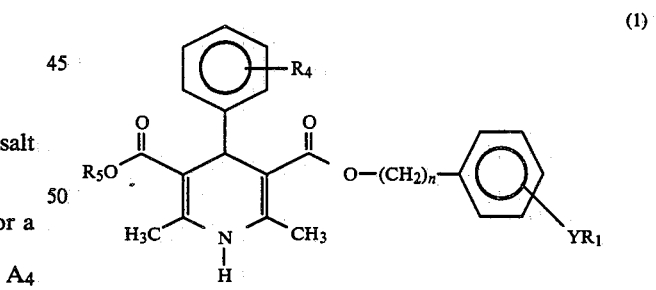

(1)

or a pharmaceutically acceptable acid addition salt thereof, wherein:
n is an integer from 0 to 8;
Y is —O, —NH, —NR$_2$, —S, —S(O), —S(O)$_2$, or a bond;
R$_1$ and R$_2$ are each independently A$_1$, A$_2$, A$_3$ or A$_4$ where:
A$_1$ is —(CH$_2$)$_m$(CHOH)$_p$CH$_2$OH;
A$_2$ is —(CH$_2$)$_q$CH$_{(3-r)}$[(CH$_2$)$_s$OH]$_r$;
A$_3$ is —(CH$_2$)$_q$CH$_{(3-r)}$[(CH$_2$)$_p$COOR$_3$]$_r$; and
A$_4$ is —(CH$_2$)$_m$COOR$_3$; where
m is an integer from 1 to 8;
p is an integer from 0 to 4;
q is an integer from 0 to 8;

r is 2 or 3;

s is an integer from 1 to 4; and $R_3$ is H or alkyl of 1 to 18 carbon atoms;

$R_4$ is —$NO_2$, —$CF_3$, or halo; and $R_5$ is lower alkyl or —$CH_2CH_2OCH_3$.

16. The method of claim 15 wherein the compound is 2,6-dimethyl-3-methoxycarbonyl-4-(3-nitrophenyl)-5-(2-[4-(2,3-dihydroxypropoxy)phenyl]ethoxycarbonyl)-1,4-dihydropyridine.

17. The method of claim 15 wherein the compound is 2,6-dimethyl-3-methoxycarbonyl-4-(3-nitrophenyl)-5-[4-(2,3-dihydroxypropoxy)phenyl]methoxycarbonyl)-1,4-dihydropyridine.

18. The method of claim 15 wherein the compound is 2,6-dimethyl-3-methoxycarbonyl-4-(3-nitrophenyl)-5-(3-[4-(2,3-dihydroxypropoxy)phenyl]propoxycarbonyl)-1,4-dihydropyridine.

19. The method of claim 15 wherein the compound is 2,6-dimethyl-3-methoxycarbonyl-4-(3-nitrophenyl)-5-(2-[4-(1,3-dihydroxyprop-2-oxy)phenyl]ethoxycarbonyl)-1,4-dihydropyridine.

20. The method of claim 15 wherein the compound is 2,6-dimethyl-3-methoxycarbonyl-4-(3-nitrophenyl)-5-(2-[4-(2-hydroxyethylamino)phenyl]ethoxycarbonyl)-1,4-dihydropyridine hydrochloride.

21. The method of claim 15 wherein the compound is 2,6-dimethyl-3-methoxycarbonyl-4-(3-nitrophenyl)-5-(2-[4-N,N-(2-hydroxyethyl)aminophenyl]ethoxycarbonyl)-1,4-dihydropyridine hydrochloride.

22. The method of claim 15 wherein the compound is 2,6-dimethyl-3-methoxycarbonyl-4-(3-nitrophenyl)-5-[2-(4-methoxycarbonylmethoxyphenyl)ethoxycarbonyl]-1,4-dihydropyridine.

23. The method of claim 15 wherein the compound is 2,6-dimethyl-3-methoxycarbonyl-4-(3-nitrophenyl)-5-[2-(4-aminophenyl)ethoxycarbonyl]-1,4-dihydropyridine hydrochloride.

* * * * *